United States Patent [19]

Allen et al.

[11] Patent Number: 5,324,729
[45] Date of Patent: Jun. 28, 1994

[54] SUBSTITUTED PYRIMIDINES, PYRIMIDINONES AND PYRIDOPYRIMIDINES

[75] Inventors: Eric E. Allen, Edison; William J. Greenlee, Teaneck; Malcolm MacCoss, Freehold; Arthur A. Patchett, Westfield, all of N.J.

[73] Assignee: Merck & Co., Inc., Rahway, N.J.

[21] Appl. No.: 908,143

[22] Filed: Jul. 31, 1992

Related U.S. Application Data

[60] Division of Ser. No. 676,158, Mar. 27, 1991, Pat. No. 5,166,206, which is a continuation-in-part of Ser. No. 501,580, Mar. 30, 1990, abandoned.

[51] Int. Cl.$^5$ ................. C07D 471/04; C07D 403/10; A61K 31/505
[52] U.S. Cl. ...................... 514/258; 514/80; 544/282; 544/244
[58] Field of Search ............... 544/282, 244; 514/258, 514/80

[56] References Cited

U.S. PATENT DOCUMENTS 5,166,206  11/1992  Allen et al. ............ 544/310

FOREIGN PATENT DOCUMENTS

58696/90   1/1991   Australia .
0424317A2  10/1989  European Pat. Off. .
0435827A2  12/1989  European Pat. Off. .
91/15209   10/1991  World Int. Prop. O. .

Primary Examiner—John M. Ford
Attorney, Agent, or Firm—Valerie J. Camara; Mark R. Daniel; Joseph F. DiPrima

[57] ABSTRACT

Substituted pyrimidines, pyrimidinones and pyridopyrimidines of formula (I) are as angiotensin II antagonists useful in the treatment of hypertension, ocular hypertension and certain CNS ailments:

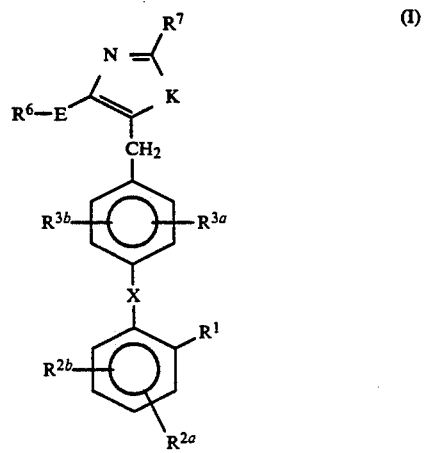

wherein K is $-N(R^{8a})-C(=M)$ or $-N=C(R^{8b})$ where M is O or $NR^{22}$.

14 Claims, No Drawings

SUBSTITUTED PYRIMIDINES, PYRIMIDINONES AND PYRIDOPYRIMIDINES

CROSS-REFERENCE TO RELATED APPLICATIONS

The instant case is a divisional application of U.S. patent application Ser. No. 07/676,158, filed Mar. 27, 1991, which issued as U.S. Pat. No. 5,166,206 on Nov. 24, 1992, which in turn is a continuation-in-part application of U.S. patent application Ser. No. 07/501,580, filed Mar. 30, 1990, now abandoned.

SUMMARY OF THE INVENTION

This invention relates to novel substituted pyrimidine, pyrimidinone and pyridopyrimidine compounds and derivatives thereof which are useful as angiotensin II antagonists in the treatment of elevated blood pressure and congestive heart failure. The compounds of the invention are also useful as ocular antihypertensives.

The compounds of this invention also have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS•A II is a powerful arterial vasoconstrictor that exerts its action by interacting with specific receptors present on cell membranes. One of the possible modes of controlling the BAS is angiotensin II receptor antagonism. Several peptide analogs of AII are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; and 4,582,847; in European Patent Applications 028,834; 245,637; 253,310; 291,969; 323,841; and 324,377; and in articles by A. T. Chiu, et al. [*Eur. J. Pharm. Exp. Therap*, 157, 13–21 (1988)] and by P. C. Wong, et al. [*J. Pharm. Exp. Therap*, 247, 1-7(1988)3. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted pyrimidine, pyrimidinone and pyridopyrimidine compounds and derivatives thereof which are useful as angiotensin II antagonists, as antihypertensives, in the treatment of congestive heart failure and in the treatment of elevated intraocular pressure. The compounds of this invention have the general formula (I):

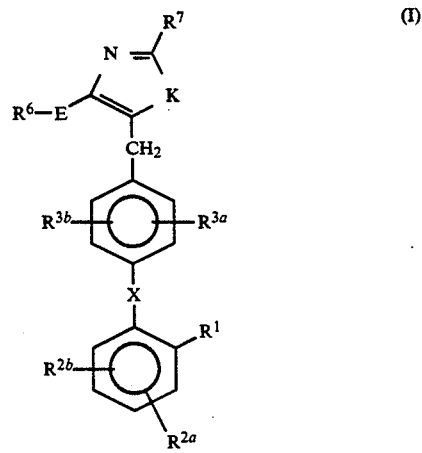

wherein:

K is $-N(R^{8a})-C(=M)$ or $-N=C(R^{8b})$-wherein M is O or $NR^{22}$.

Thus, the compounds of formula I can also be expressed as compounds having the following formulae (Ia), (Ib), and (Ic) if $R^7$ and $R^{8a}$ are joined)

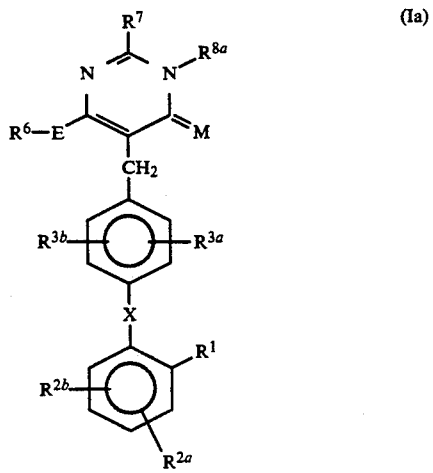

-continued

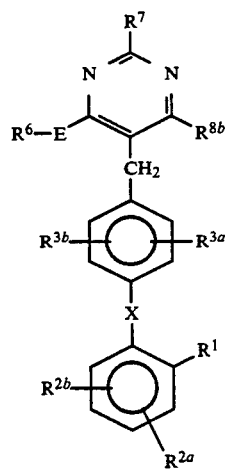

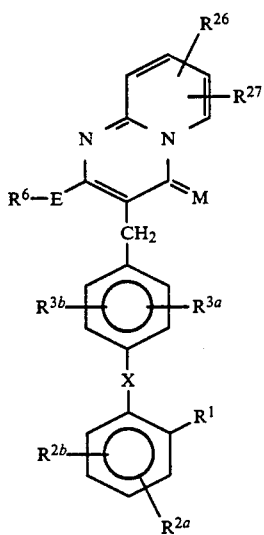

wherein:
R¹ is
(a) —$CO_2R^4$,
(b) —$SO_3R^5$,
(c) —$NHSO_2(C_1-C_4$-polyfluoroalkyl)
(d) —$PO(OR^5)_2$,
(e) —$SO_2$—NH—$R^9$,
(f) —$CONHOR^5$,

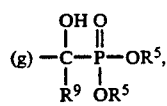

(h) —CN,
(i) —$SO_2$NH-heteroaryl,
(j) —$CH_2SO_2$NH-heteroaryl,
(k) —$SO_2$NH—CO—$R^{23}$,
(l) —$CH_2SO_2$NH—CO—$R^{23}$,
(m) —CONH—$SO_2R^{23}$,
(n) —$CH_2$CONH—$SO_2R^{23}$,
(o) —$NHSO_2$NHCO—$R^{23}$,
(p) —NHCONHSO_2—$R^{23}$,

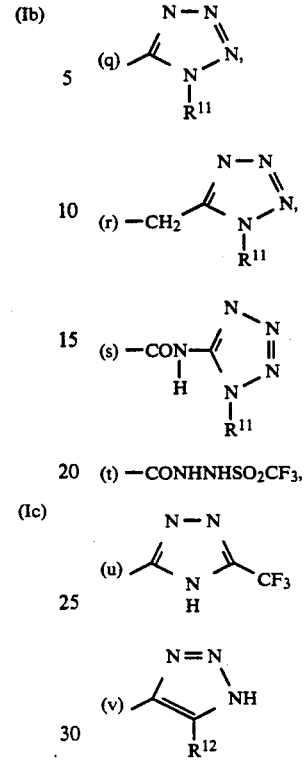

(t) —$CONHNHSO_2CF_3$, wherein heteroaryl is an unsubstituted, monosubstituted or disubstituted five or six membered aromatic fine comprising from 1 to 3 heteroatoms selected from the group consisting of O, N or S and wherein the substituents are members selected from the group consisting of —OH, —SH, —$C_1$–$C_4$-alkyl, —$C_1$–$C_4$-alkoxy, —$CF_3$, Cl, Br, F, I, —$NO_2$, —$CO_2$H, —$CO_2$, $C_1$–$C_4$-alkyl, —$NH_2$, NH($C_1$-$C_4$-alkyl) and —N($C_1$-$C_4$-alkyl)$_2$;
$R^{2a}$ and $R^{2b}$ are each independently
(a) H,
(b) Cl, Br, I or F,
(c) $NO_2$,
(d) $NH_2$,
(e) $C_1$-$C_4$-alkylamino,
(f) di-($C_1$-$C_4$-alkyl)amino
(g) $SO_2NHR^9$,
(h) $CF_3$,
(i) $C_1$-$C_4$-alkyl, or
(j) $C_1$-$C_4$-alkoxy;
$R^{3a}$ is
(a) H,
(b) Cl, Br, I, F
(c) $C_1$-$C_6$-alkyl,
(d) $C_1$-$C_6$-alkoxy,
(e) $C_1$-$C_6$-alkoxy-$C_1$-$C_4$-alkyl;
$R^{3b}$ is
(a) H,
(b) Cl, Br, I, F
(c) $NO_2$,
(d) $C_1$-$C_6$-alkyl,
(e) $C_2$-$C_6$-alkanoyloxy,
(f) $C_3$-$C_6$-cycloalkyl,
(g) $C_1$-$C_6$-alkoxy,
(h) —$NHSO_2R^4$,
(i) hydroxy-$C_1$-$C_4$-alkyl, (j) aryl-$C_1$-$C_4$-alkyl,
(k) $C_1$-$C_4$-alkylthio,
(l) $C_1$-$C_4$-alkylsulfinyl,
(m) $C_1$-$C_4$-alkylsulfonyl,
(n) $NH_2$,
(o) $C_1$-$C_4$-alkylamino,
(p) $C_1$-$C_4$-dialkylamino,
(q) $CF_3$,
(r) —$SO_2$—$NHR^9$,
(s) aryl or
(t) furyl;

wherein aryl is phenyl or naphthyl unsubstituted or substituted with one or two substituents selected from the group consisting of Cl, Br, I, F, $C_1$-$C_4$-alkyl, $C_1$-$C_4$-alkoxy, $NO_2$, $CF_3$, $C_1$-$C_4$-alkylthio, OH, $NH_2$, —NH(-$C_1$-$C_4$-alkyl), —N($C_1$-$C_4$-alkyl)$_2$, —$CO_2H$, $C_1$-$C_4$ polyfluoroalkyl, $C_3$-$C_6$-polyfluorocycloalkyl, —$CO_2$-$C_1$-$C_4$-alkyl or

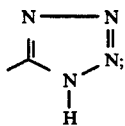

$R^4$ is H, $C_1$-$C_6$-alkyl, benzyl or phenyl;
$R^5$ is H,

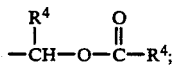

E is a single bond, —$NR^{13}(CH_2)_s$—, —$S(O)_x(CH_2)_s$—where x is 0 to 2 and s is 0 to 5, —CH(OH)—, —O—, —CO—;

$R^6$ is
(a) $C_1$-$C_6$-alkyl, $C_2$-$C_5$-alkenyl or $C_2$-$C_5$-alkynyl each of which can be substituted with a substituent selected from the group consisting of aryl, $C_3$-$C_7$-cycloalkyl, Cl, Br, I, F, —OH, $CF_3$, $CCl_3$, —$NH_2$, —NH($C_1$-$C_4$-alkyl), —N($C_1$-$C_4$-alkyl)$_2$, —NH—$SO_2R_4$, —$COOR^4$, —$SO_2NHR^9$, $C_1$-$C_4$-alkoxy, $C_1$-$C_4$-alkyl-S, —$CF_2CF_3$;
(b) $C_3$-$C_5$-cycloalkyl;
(c) polyfluoro-$C_1$-$C_4$-alkyl;

$R^7$ is
(a) hydrogen,
(b) aryl,
(c) heteroaryl,
(d) Cl, Br, I, F,
(e) —$CO_2H$,
(f) —$CO_2R_4$,
(g) —$NH_2$,
(h) —NH($C_1$-$C_4$-alkyl),
(i) —N($C_1$-$C_4$-alkyl)$_2$,
(j) —$SO_2NR^9R^{10}$,
(k) —$NHSO_2$-$C_1$-$C_4$-alkyl,
(l) —$S(O)_x$-$C_1$-$C_4$-alkyl,
(m) —OH,
(n) —SH,
(o) —$S(O)_x$-aryl,
(p) —$C_1$-$C_4$-alkyl or —O($C_1$-$C_4$-alkyl) or —S(-$C_1$-$C_4$-alkyl) each of which can be substituted with aryl, heteroaryl, —OH, —$NH_2$, —$CF_3$, $C_3$-$C_5$-cycloalkyl, —NH($C_1$-$C_4$-alkyl), —N($C_1$-$C_4$-alkyl)$_2$, —$CO_2H$, —$CO_2R^4$, Cl, Br, I, or F,
(q) $C_3$-$C_5$-cycloalkyl or
(r) —$CF_3$;

$R^{8a}$ is
(a) aryl,
(b) heteroaryl,
(c) $C_1$-$C_4$-alkyl either unsubstituted or substituted with aryl, heteroaryl, —OH, —$NH_2$, —NH($C_1$-$C_4$-alkyl), N($C_1$-$C_4$-alkyl)$_2$, —$CO_2H$, —$CO_2R^4$ Cl, Br, I, or F, or
(d) $C_1$-$C_4$-alkylaryl either unsubstituted or substituted with $CO_2R^4$; or $R^7$ and $R^{8a}$ when alkyl groups on adjacent atoms may be joined together with the atoms to which they are bound to form a pyridine ring which may be unsubstituted or substituted with $R^{26}$ or $R^{27}$ or $R^{26}$ and $R^{27}$ wherein $R^{26}$ is
(a) $R^7$
(b) —NHCO($C_1$-$C_5$-alkyl),
(c) —NHCO($C_3$-$C_6$-cycloalkyl),
(d) —NHCO(aryl),
(e) —NHCO(heteroaryl),
(f) —N($C_1$-$C_5$-alkyl)CO($C_1$-$C_5$-alkyl),
(g) —N($C_1$-$C_5$-alkyl)CO($C_3$-$C_6$-cycloalkyl),
(h) —N($C_1$-$C_5$-alkyl)CO(aryl),
(i) —N($C_1$-$C_5$-alkyl)CO(heteroaryl) and $R^{27}$ is $C_1$-$C_4$-alkyl, Cl, Br, F, I, —$CF_3$, aryl or heteroaryl $R^{8b}$ is (a) —OH,
(b) —$NH_2$,
(c) —NH($C_1$-$C_4$-alkyl),
(d) —N($C_1$-$C_4$-alkyl)$_2$,
(e) —$NHCO_2$-$C_1$-$C_4$-alkyl,
(f) —NHCO-$C_1$-$C_4$-alkyl,
(g) —$NHSO_2$-$C_1$-$C_4$-alkyl,
(h) —$NHSO_2$-aryl,
(i) —$NHSO_2$($C_1$-$C_4$-polyfluoroalkyl),
(j) —$CO_2H$,
(k) —$CO_2R^4$,
(l) Cl, Br, I, F,
(m) —$CONHSO_2$-aryl,
(n) —$CONHSO_2$-heteroaryl,
(o) —$CONHSO_2$-$C_1$-$C_4$-alkyl,
(p) —$CONHSO_2$-($C_1$-$C_4$-polyfluoroalkyl),
(q) —$CH_2OCOR^4$,
(r) —$CH_2OCOR^4$,
(s) —O-$C_1$-$C_4$-alkyl, unsubstituted or substituted with $CO_2R_4$,
(t) —$S(O)_x$—$C_1$-$C_4$-aryl unsubstituted or substituted with $CO_2R^4$,
(u) —$S(O)_x$—$C_1$-$C_4$-alkyl unsubstituted or substituted with $CO_2R^4$,
(v) —$SO_2NHR^{25}$,
(w) —CN,
(x) tetrazol-5-yl;

$R^9$ is H, $C_1$-$C_5$-alkyl, phenyl or benzyl;
$R^{10}$ is H, $C_1$-$C_4$-alkyl;
$R^{11}$ is H, $C_1$-$C_6$-alkyl, $C_2$-$C_4$-alkenyl, $C_1$-$C_4$-alkoxy alkyl, or —$CH_2$-$C_6H_4R^{20}$;
$R^{12}$ is —CN, —$NO_2$, —$CO_2R^4$, or —$CF_3$;
$R^{13}$ is H, $C_2$-$C_4$-alkanoyl, $C_1$-$C_6$-alkyl, allyl, $C_3$-$C_6$-cycloalkyl, phenyl or benzyl;
$R^{14}$ is H, $C_1$-$C_8$-alkyl, $C_1$-$C_8$-perfluoroalkyl, $C_3$-$C_6$-cycloalkyl, phenyl or benzyl;
$R^{15}$ is H, $C_1$-$C_6$-alkyl;
$R^{16}$ is H, $C_1$-$C_6$-alkyl, $C_3$-$C_6$-cycloalkyl, phenyl or benzyl;
$R^{17}$ is —$NR^9R^{10}$, —$NHCONH_2$, —$NHCSNH_2$,

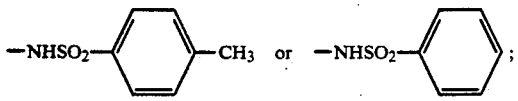

R$^{18}$ and R$^{19}$ are independently C$_1$–C$_4$-alkyl or taken together are —(CH$_2$)$_q$- where q is 2 or 3;

R$^{20}$ is H, —NO$_2$, —NH$_2$, —OH or —OCH$_3$;

R$^{21}$ is (a) —CO-aryl (b) —CO—C$_1$–C$_4$-alkyl, (c) —COCF$_3$, (d) —CO-heteroaryl, (e) heteroaryl;

R$^{22}$ is the same as R$^{8a}$ or —H;

R$^{23}$ is (a) aryl, (b) heteroaryl, (c) C$_3$–C$_7$-cycloalkyl, (d) C$_1$–C$_6$-alkyl unsubstituted or substituted with a substituent selected from the group consisting of aryl, heteroaryl, —OH, —SH, —C$_1$–C$_4$-alkyl, —O(C$_1$–C$_4$-alkyl), —S(C$_1$–C$_4$-alkyl —CF$_3$, Cl, Br, F, or I, —NO$_2$, —CO$_2$H, —CO$_2$—C$_1$–C$_4$-alkyl, —NH$_2$, —NH(C$_1$–C$_4$-alkyl), —N(C$_1$–C$_4$-alkyl)$_2$, —PO$_3$H$_2$, or —PO(OH)(O—C$_1$–C$_4$-alkyl);

R$^{25}$ is (a) H, (b) C$_1$–C$_4$-alkyl;

X is (a) a carbon-carbon single bond, (b) —CO—, (c) —O—, (d) —S—, (e) —N—
    |
    R$^{13}$ (f) —CON—
     |
     R$^{15}$ (g) —NCO—
    |
    R$^{15}$ (h) —OCH$_2$—, (i) —CH$_2$O—

(j) —SCH$_2$—, (k) —CH$_2$S—, (l) —NHC(R$^9$)(R$^{10}$)—, (m) —NR$^9$SO$_2$—, (n) —SO$_2$NR$^9$—, (o) —C(R$^9$)(R$^{10}$)NH—, (p) —CH=CH—, (q) —CF=CF—, (r) —CH=CF—, (s) —CF=CH—, (t) —CH$_2$CH$_2$—, (u) —CF$_2$CF$_2$—,

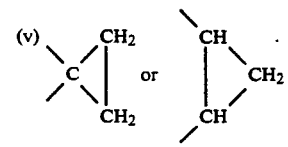

(w) —CH—,
    |
    OR$^{14}$ (x) —CH—,
    |
    OCOR$^{16}$ (y) —C—, or
    ‖
    NR$^{17}$ (z) 
  R$^{18}$O\  /OR$^{19}$
     C
     |

Z is O, NR$^{13}$ or S; or, a pharmaceutically acceptable salt thereof.

The terms "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

One embodiment of the novel compounds is that of formula Ib wherein K is —N=C(R$^{8b}$)

In a class of this embodiment,

R$^1$ is —COOH;

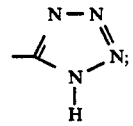

—NH—SO$_2$CF$_3$; —CO$_2$R$^4$;

—SO$_2$NH- heteroaryl or CH$_2$SO$_2$NH—heteroaryl wherein the heteroaryl is an unsubstituted, monosubstituted or disubstituted 5- or 6-membered aromatic ring 1 to 3 heteroatoms selected from O, N and S and wherein the substituents are members selected from the group consisting of OH, SH, C$_1$–C$_4$-alkyl, C$_1$–C$_4$-alkoxy, CF$_3$, Cl, Br, F, I, NO$_2$, CO$_2$H, CO$_2$—C$_1$–C$_4$-alkyl, NH$_2$, NH(C$_1$–C$_4$-alkyl) and N(C$_1$–C$_4$-alkyl)$_2$; —SO$_2$NH-COR$^{23}$;—CH$_2$SO$_2$NHCOR$^{23}$; —CONHSO$_2$R$^{23}$; —CH$_2$CONHSO$_2$R$^{23}$; —NHSO$_2$NHCOR$^{23}$; or —NH-CONHSO$_2$R$^{23}$;

R$^{2a}$ and R$^{2b}$ are H, F, Cl, CF$_3$, C$_1$–C$_4$-alkyl or C$_1$–C$_4$-alkoxy;

R$^{3a}$ is H, F or Cl;

R$^{3b}$ is H, F, Cl, CF$_3$, C$_1$–C$_4$-alkyl, C$_1$–C$_4$-alkoxy, —COOCH$_3$, —COOC$_2$H$_5$, —SO$_2$—CH$_3$, NH$_2$, —N(C$_1$–C$_4$-alkyl)$_2$ or —NH—SO$_2$CH$_3$;

E is a single bond, —O—or —S—;

R$^6$ is (a) C$_1$–C$_5$-alkyl, C$_2$–C$_5$-alkenyl or C$_2$–C$_5$-alkynyl each of which can be substituted with a substituent selected from the group consisting of, CF$_3$, CF$_2$CF$_3$, —O—CH₃, —OC₂H₅, —S—CH₃, —S—C₂H₅, phenyl and C₃-C₅-cycloalkyl;
(b) C₃-C₅-cycloalkyl; and
(c) polyfluoro-C₁-C₄-alkyl;
X is a C—C single bond.

In a more preferred class of this embodiment are those compounds wherein:
E is a single bond;
$R^{2a}$, $R^{2b}$, $R^{3a}$ and $R^{3b}$ are each H; and
X is a single bond.
Exemplifying this embodiment are the following compounds of the Formula II shown in Table 1:

TABLE 1

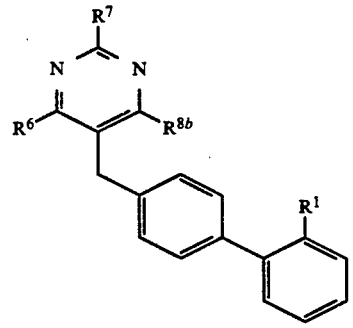

II

| Compd. No. | R¹ | R⁶ | R⁷ | R⁸ᵇ |
|---|---|---|---|---|
| II-1 | tetrazol-5-yl | Bu | Me | —COOMe |
| II-2 | tetrazol-5-yl | Bu | Me | —COOEt |
| II-3 | tetrazol-5-yl | Bu | Me | —COOH |
| II-4 | tetrazol-5-yl | Bu | Me | —CHO |
| II-5 | tetrazol-5-yl | Bu | Me | —CH₂OH |
| II-6 | tetrazol-5-yl | Bu | Me | —NHSO₂CF₃ |
| II-7 | tetrazol-5-yl | Bu | Me | —NHSO₂CF₂CF₃ |
| II-8 | tetrazol-5-yl | Bu | Me | —NHSO₂Ph |
| II-9 | tetrazol-5-yl | Bu | Me | —CONHSO₂Ph |
| II-10 | tetrazol-5-yl | Bu | Me | —SO₂NHCOcyPr |
| II-11 | tetrazol-5-yl | Bu | Me | —SO₂NHSO₂CF₃ |
| II-12 | tetrazol-5-yl | Pr | Me | —COOMe |
| II-13 | tetrazol-5-yl | Pr | Me | —COOEt |
| II-14 | tetrazol-5-yl | Pr | Me | —COOH |
| II-15 | tetrazol-5-yl | Pr | Me | —CHO |
| II-16 | tetrazol-5-yl | Pr | Me | —CH2OH |
| II-17 | tetrazol-5-yl | Pr | Me | —NHSO₂CF₃ |
| II-18 | tetrazol-5-yl | Pr | Me | —NHSO₂CF₂CF₃ |
| II-19 | tetrazol-5-yl | Pr | Me | —NHSO₂Ph |
| II-20 | tetrazol-5-yl | Pr | Me | —CONHSO₂Ph |
| II-21 | tetrazol-5-yl | Pr | Me | —SO₂NHCOcyPr |
| II-22 | tetrazol-5-yl | Pr | Me | —SO₂NHSO₂CF₃ |
| II-23 | —NHSO₂CF₃ | Bu | Me | —COOMe |
| II-24 | —NHSO₂CF₃ | Bu | Me | —COOEt |
| II-25 | —NHSO₂CF₃ | Bu | Me | —COOH |
| II-26 | —NHSO₂CF₃ | Bu | Me | —CHO |
| II-27 | —NHSO₂CF₃ | Bu | Me | —CH₂OH |
| II-28 | —NHSO₂CF₃ | Bu | Me | —NHSO₂CF₃ |
| II-29 | —NHSO₂CF₃ | Bu | Me | —NHSO₂CF₂CF₃ |
| II-30 | —NHSO₂CF₃ | Bu | Me | —NHSO₂Ph |
| II-31 | —NHSO₂CF₃ | Bu | Me | —CONHSO₂Ph |
| II-32 | —NHSO₂CF₃ | Bu | Me | —SO₂NHCOcyPr |
| II-33 | —NHSO₂CF₃ | Bu | Me | —SO₂NHSO₂CF₃ |
| II-34 | —NHSO₂CF₃ | Pr | Me | —COOMe |
| II-35 | —NHSO₂CF₃ | Pr | Me | —COOEt |
| II-36 | —NHSO₂CF₃ | Pr | Me | —COOH |
| II-37 | —NHSO₂CF₃ | Pr | Me | —CHO |
| II-38 | —NHSO₂CF₃ | Pr | Me | —CH₂OH |
| II-39 | —NHSO₂CF₃ | Pr | Me | —NHSO₂CF₃ |
| II-40 | —NHSO₂CF₃ | Pr | Me | —NHSO₂CF₂CF₃ |
| II-41 | —NHSO₂CF₃ | Pr | Me | —NHSO₂Ph |
| II-42 | —NHSO₂CF₃ | Pr | Me | —CONHSO₂Ph |
| II-43 | —NHSO₂CF₃ | Pr | Me | —SO₂NHCOcyPr |
| II-44 | —NHSO₂CF₃ | Pr | Me | —SO₂NHSO₂CF₃ |
| II-45 | —SO₂NHCOcyPr | Bu | Me | —COOMe |
| II-46 | —SO₂NHCOcyPr | Bu | Me | —COOEt |
| II-47 | —SO₂NHCOcyPr | Bu | Me | —COOH |
| II-48 | —SO₂NHCOcyPr | Bu | Me | —CHO |
| II-49 | —SO₂NHCOcyPr | Bu | Me | —CH₂OH |
| II-50 | —SO₂NHCOcyPr | Bu | Me | —NHSO₂CF₃ |
| II-51 | —SO₂NHCOcyPr | Bu | Me | —NHSO₂CF₂CF₃ |
| II-52 | —SO₂NHCOcyPr | Bu | Me | —NHSO₂Ph |
| II-53 | —SO₂NHCOcyPr | Bu | Me | —CONHSO₂Ph |
| II-54 | —SO₂NHCOcyPr | Bu | Me | —SO₂NHCOcyPr |

TABLE 1-continued

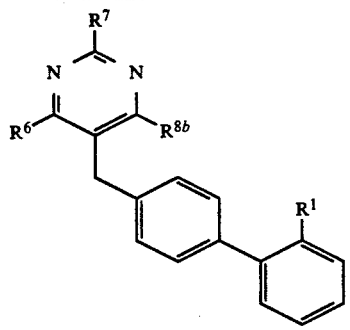

| Compd. No. | R¹ | R⁶ | R⁷ | R⁸ᵇ |
|---|---|---|---|---|
| II-55 | —SO₂NHCOᶜʸPr | Bu | Me | —SO₂NHSO₂CF₃ |
| II-56 | —SO₂NHCOᶜʸPr | Pr | Me | —COOMe |
| II-57 | —SO₂NHCOᶜʸPr | Pr | Me | —COOEt |
| II-58 | —SO₂NHCOᶜʸPr | Pr | Me | —COOH |
| II-59 | —SO₂NHCOᶜʸPr | Pr | Me | —CHO |
| II-60 | —SO₂NHCOᶜʸPr | Pr | Me | —CH₂OH |
| II-61 | —SO₂NHCOᶜʸPr | Pr | Me | —NHSO₂CF₃ |
| II-62 | —SO₂NHCOᶜʸPr | Pr | Me | —NHSO₂CF₂CF₃ |
| II-63 | —SO₂NHCOᶜʸPr | Pr | Me | —NHSO₂Ph |
| II-64 | —SO₂NHCOᶜʸPr | Pr | Me | —CONHSO₂Ph |
| II-65 | —SO₂NHCOᶜʸPr | Pr | Me | —SO₂NHCOᶜʸPr |
| II-66 | —SO₂NHCOᶜʸPr | Pr | Me | —SO₂NHSO₂CF₃ |
| II-67 | tetrazol-5-yl | Pr | —CF₂CF₃ | —COOMe |
| II-68 | tetrazol-5-yl | Pr | —CF₂CF₃ | —COOEt |
| II-69 | tetrazol-5-yl | Pr | —CF₂CF₃ | —COOH |
| II-70 | tetrazol-5-yl | Pr | —CF₂CF₃ | —CHO |
| II-71 | tetrazol-5-yl | Pr | —CF₂CF₃ | —CH₂OH |
| II-72 | tetrazol-5-yl | Pr | —CF₂CF₃ | —NHSO₂CF₃ |
| II-73 | tetrazol-5-yl | Pr | —CF₂CF₃ | —NHSO₂CF₂CF₃ |
| II-74 | tetrazol-5-yl | Pr | —CF₂CF₃ | —NHSO₂Ph |
| II-75 | tetrazol-5-yl | Pr | —CF₂CF₃ | —CONHSO₂Ph |
| II-76 | tetrazol-5-yl | Pr | —CF₂CF₃ | —SO₂NHCOᶜʸPr |
| II-77 | tetrazol-5-yl | Pr | —CF₂CF₃ | —SO₂NHSO₂CF₃ |
| II-78 | —NHSO₂CF₃ | Pr | —CF₂CF₃ | —COOMe |
| II-79 | —NHSO₂CF₃ | Pr | —CF₂CF₃ | —COOEt |
| II-80 | —NHSO₂CF₃ | Pr | —CF₂CF₃ | —COOH |
| II-81 | —NHSO₂CF₃ | Pr | —CF₂CF₃ | —CHO |
| II-82 | —NHSO₂CF₃ | Pr | —CF₂CF₃ | —CH₂OH |
| II-83 | —NHSO₂CF₃ | Pr | —CF₂CF₃ | —NHSO₂CF₃ |
| II-84 | —NHSO₂CF₃ | Pr | —CF₂CF₃ | —NHSO₂CF₂CF₃ |
| II-85 | —NHSO₂CF₃ | Pr | —CF₂CF₃ | —NHSO₂Ph |
| II-86 | —NHSO₂CF₃ | Pr | —CF₂CF₃ | —CONHSO₂Ph |
| II-87 | —NHSO₂CF₃ | Pr | —CF₂CF₃ | —SO₂NHCOᶜʸPr |
| II-88 | —NHSO₂CF₃ | Pr | —CF₂CF₃ | —SO₂NHSO₂CF₃ |
| II-89 | —SO₂NHCOᶜʸPr | Pr | —CF₂CF₃ | —COOMe |
| II-90 | —SO₂NHCOᶜʸPr | Pr | —CF₂CF₃ | —COOEt |
| II-91 | —SO₂NHCOᶜʸPr | Pr | —CF₂CF₃ | —COOH |
| II-92 | —SO₂NHCOᶜʸPr | Pr | —CF₂CF₃ | —CHO |
| II-93 | —SO₂NHCOᶜʸPr | Pr | —CF₂CF₃ | —CH₂OH |
| II-94 | —SO₂NHCOᶜʸPr | Pr | —CF₂CF₃ | —NHSO₂CF₃ |
| II-95 | —SO₂NHCOᶜʸPr | Pr | —CF₂CF₃ | —NHSO₂CF₂CF₃ |
| II-96 | —SO₂NHCOᶜʸPr | Pr | —CF₂CF₃ | —NHSO₂Ph |
| II-97 | —SO₂NHCOᶜʸPr | Pr | —CF₂CF₃ | —CONHSO₂Ph |
| II-98 | —SO₂NHCOᶜʸPr | Pr | —CF₂CF₃ | —SO₂NHCOᶜʸPr |
| II-99 | —SO₂NHCOᶜʸPr | Pr | —CF₂CF₃ | —SO₂NHSO₂CF₃ |
| II-100 | —SO₂NHCOPh | Pr | Me | —COOMe |
| II-101 | —SO₂NHCOPh | Pr | —CF₂CF₃ | —COOMe |
| II-102 | —SO₂NHCO—(CH₂)₅NH₂ | Pr | Me | —COOMe |
| II-103 | —SO₂NHCO—(CH₂)₅NH₂ | Pr | —CF₂CF₃ | —COOMe |
| II-104 | —SO₂NHCOPh | Pr | Me | —NHSO₂CF₃ |
| II-105 | —SO₂NHCOPh | Pr | —CF₂CF₃ | —SO₂NHCOᶜʸPr |
| II-106 | —SO₂NHCO—(CH₂)₅NH₂ | Pr | Me | —NHSO₂CF₃ |
| II-107 | —SO₂NHCO—(CH₂)₅NH₂ | Pr | —CF₂CF₃ | —SO₂NHCOᶜʸPr |

In another embodiment of the novel compounds is that of formula Ia (M=O) wherein K is —N(-R⁸ᵃ)—CO—.

In a class of this embodiment
R¹ is —COOH;

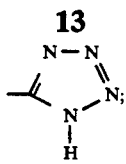

—NH—SO₂CF₃; CO₂R⁴; —SO₂NH—heteroaryl or CH₂SO₂NH—heteroaryl wherein the heteroaryl is an unsubstituted, monosubstituted or disubstituted 5- or 6-membered aromatic ring comprising contain 1 to 3 heteroatoms selected from O, N and S and wherein the substituents are members selected from the group consisting of OH, SH, C₁-C₄-alkyl, C₁-C₄-alkoxy, CF₃, Cl, Br, F, I, NO₂, CO₂H CO₂—C₁-C₄-alkyl, NH₂, NH(C₁-C₄-alkyl) and N(C₁-C₄-alkyl)₂; —SO₂NH-COR²³; —CH₂SO₂NHCOR²³; —CONHSO₂R²³; —CH2CONHSO₂R²³; —NHSO₂NHCOR²³; and —NHCONHSO₂R²³;

R²ᵃ and R²ᵇ are H, F, el, CF₃, C₁-C₄-alkyl or C₁-C₄-alkoxy;

R³ᵃ is H, F or Cl;

R³ᵇ is H, F, Cl, CF₃, C₁-C₄-alkyl, C₁-C₄-alkoxy, —COOCH₃, —COOC₂H₅, —SO₂—CH₃, NH₂, —N(-C₁-C₄-alkyl)₂ or —NH—SO₂CH₃;

E is a single bond, —O— or —S—;

R⁶ is
(a) C₁-C₅-alkyl, C₂-C₅-alkenyl or C₂-C₅-alkynyl each of which can be substituted with a substituent selected from the group consisting of Cl, CF₃, CF₂CF₃, CCl₃, —O—CH₃, —OC₂H₅, —S—CH₃, —S—C₂H₅, phenyl and C₃-C₅-cycloalkyl;
(b) C₃-C₅-cycloalkyl;
(c) polyfluoro-C₁-C₄-alkyl;

R⁷ and R⁸ᵃ are as defined above or together with the atoms to which they are bonded may be joined to form a pyridine ring which can be substituted with R²⁶ and R²⁷; and X is a C—C single bond.

In a more preferred class of this embodiment are those compounds wherein:
E is a single bond;
R²ᵃ, R²ᵇ, R³ᵃ and R³ᵇ are each H; and
X is a single bond.

Exemplifying this embodiment are the following compounds of the Formula III shown in Table 2:

TABLE 2

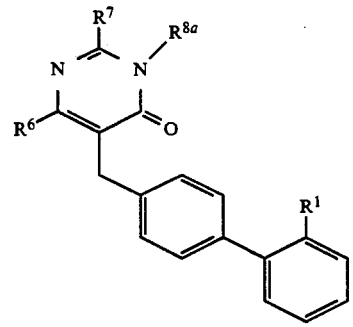

III

| Compd. No. | R¹ | R⁶ | R⁷ | R⁸ᵃ |
|---|---|---|---|---|
| III-1 | tetrazol-5-yl | Bu | Me | H |
| III-2 | tetrazol-5-yl | Pr | Me | 2-CF₃-phenyl |
| III-3 | tetrazol-5-yl | Pr | Me | 2-Cl-phenyl |
| III-4 | tetrazol-5-yl | Pr | Me | 2,6-diCl-phenyl |
| III-5 | tetrazol-5-yl | Pr | —CF₂CF₃ | 2-CF₃-phenyl |
| III-6 | tetrazol-5-yl | Pr | —CF₂CF₃ | 2-Cl-phenyl |
| III-7 | tetrazol-5-yl | Pr | Me | 2-COOH-phenyl |
| III-8 | tetrazol-5-yl | Pr | Me | —CF₂CF₃ |
| III-9 | —NHSO₂CF₃ | Bu | Me | H |
| III-10 | —NHSO₂CF₃ | Pr | Me | 2-CF₃phenyl |
| III-11 | —NHSO₂CF₃ | Pr | Me | 2-Cl-phenyl |
| III-12 | —NHSO₂CF₃ | Pr | Me | 2,6-diCl-phenyl |
| III-13 | —NHSO₂CF₃ | Pr | —CF₂CF₃ | 2-CF₃-phenyl |
| III-14 | —NHSO₂CF₃ | Pr | —CF₂CF₃ | 2-Cl-phenyl |
| III-15 | —NHSO₂CF₃ | Pr | Me | 2-COOH-phenyl |
| III-16 | —NHSO₂CF₃ | Pr | Me | —CF₂CF₃ |
| III-17 | —SO₂NHCOⁿPr | Pr | Me | 2-CF₃-phenyl |
| III-18 | —SO₂NHCOⁿPr | Pr | Me | 2-Cl-phenyl |
| III-19 | —SO₂NHCOⁿPr | Pr | Me | 2,6-diCl-phenyl |
| III-20 | —SO₂NHCOⁿPr | Pr | —CF₂CF₃ | 2-CF₃-phenyl |
| III-21 | —SO₂NHCOⁿPr | Pr | —CF₂CF₃ | 2-Cl-phenyl |
| III-22 | —SO₂NHCOⁿPr | Pr | Me | 2-COOH-phenyl |
| III-23 | —SO₂NHCOⁿPr | Pr | Me | —CF₂CF₃ |
| III-24 | SO₂NHCOPh | Pr | Me | 2-CF₃-phenyl |
| III-25 | SO₂NHCOPh | Pr | Me | 2-Cl-phenyl |
| III-26 | SO₂NHCOPh | Pr | Me | 2,6-diCl-phenyl |
| III-27 | SO₂NHCOPh | Pr | —CF₂CF₃ | 2-CF₃-phenyl |
| III-28 | SO₂NHCOPh | Pr | —CF₂CF₃ | 2-Cl-phenyl |
| III-29 | SO₂NHCOPh | Pr | Me | —CF₂CF₃ |
| III-30 | SO₂NHCOPh | Pr | Me | 2-COOH-phenyl |
| III-31 | SO₂NHCO—(CH₂)₅NH₂ | Pr | Me | 2-CF₃-phenyl |
| III-32 | SO₂NHCO—(CH₂)₅NH₂ | Pr | —CF₂CF₃ | 2-Cl-phenyl |

Also exemplifying this embodiment are the following compounds of the Formula IV shown in Table 3:

TABLE 3

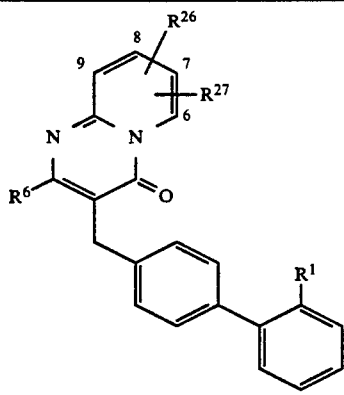

IV

| Compd. No. | R¹ | R⁶ | R²⁶ | R²⁷ |
|---|---|---|---|---|
| IV-1 | tetrazol-5-yl | Bu | H | 7-Me |
| IV-2 | tetrazol-5-yl | Bu | H | 7-$^i$Pr |
| IV-3 | tetrazol-5-yl | Pr | H | 7-N(Pen)COPh |
| IV-4 | tetrazol-5-yl | Pr | H | 7-N(Pen)CO(4-Cl—Ph) |
| IV-5 | tetrazol-5-yl | Pr | H | 7-N(Pr)CO$_2$—$^i$Bu |
| IV-6 | tetrazol-5-yl | Pr | H | 7-N(Bn)COBu |
| IV-7 | tetrazol-5-yl | Bu | 8-Cl | 7-SO$_2$Me |
| IV-8 | tetrazol-5-yl | Bu | H | 8-Cl |
| IV-9 | —NHSO$_2$CF$_3$ | Bu | H | 7-Me |
| IV-10 | —NHSO$_2$CF$_3$ | Bu | H | 7-$^i$Pr |
| IV-11 | —NHSO$_2$CF$_3$ | Pr | H | 7-N(Pen)COPh |
| IV-12 | —NHSO$_2$CF$_3$ | Pr | H | 7-N(Pen)CO(4-Cl—Ph) |
| IV-13 | —NHSO$_2$CF$_3$ | Pr | H | 7-N(Pr)CO$_2$—$^i$Bu |
| IV-14 | —NHSO$_2$CF$_3$ | Pr | H | 7-N(Bn)COBu |
| IV-15 | —NHSO$_2$CF$_3$ | Bu | 8-Cl | 7-SO$_2$Me |
| IV-16 | —NHSO$_2$CF$_3$ | Bu | H | 8-Cl |
| IV-17 | —SO$_2$NHCO-$^c$Pr | Bu | H | 7-Me |
| IV-18 | —SO$_2$NHCO-$^c$Pr | Bu | H | 7-$^i$Pr |
| IV-19 | —SO$_2$NHCO-$^c$Pr | Pr | H | 7-N(Pen)COPh |
| IV-20 | —SO$_2$NHCO-$^c$Pr | Pr | H | 7-N(Pen)CO(4-Cl—Ph) |
| IV-21 | —SO$_2$NHCO-$^c$Pr | Pr | H | 7-N(Pr)CO$_2$—$^i$Bu |
| IV-22 | —SO$_2$NHCO-$^c$Pr | Pr | H | 7-N(Bn)COBu |
| IV-23 | —SO$_2$NHCO-$^c$Pr | Bu | 8-Cl | 7-SO$_2$Me |
| IV-24 | —SO$_2$NHCO-$^c$Pr | Bu | H | 8-Cl |
| IV-25 | —SO$_2$NHCOPh | Bu | H | 7-Me |
| IV-26 | —SO$_2$NHCOPh | Bu | H | 7-$^i$Pr |
| IV-27 | —SO$_2$NHCOPh | Pr | H | 7-N(Pen)COPh |
| IV-28 | —SO$_2$NHCOPh | Pr | H | 7-N(Pen)CO(4-Cl—Ph) |
| IV-29 | —SO$_2$NHCOPh | Pr | H | 7-N(Pr)CO$_2$—$^i$Bu |
| IV-30 | —SO$_2$NHCOPh | Pr | H | 7-N(Bn)COBu |
| IV-31 | —SO$_2$NHCOPh | Bu | 8-Cl | 7-SO$_2$Me |
| IV-32 | —SO$_2$NHCOPh | Bu | H | 8-Cl |
| IV-33 | —SO$_2$NHCO—(CH$_2$)$_5$NH$_2$ | Bu | H | 7-$^i$Pr |
| IV-34 | —SO$_2$NHCO—(CH$_2$)$_5$NH$_2$ | Bu | 8-Cl | 7-SO$_2$Me |
| IV-35 | —SO$_2$NHCO—(CH$_2$)$_5$NH$_2$ | Bu | H | 8-Cl |
| IV-36 | —SO$_2$NHCO—(CH$_2$)$_5$NH$_2$ | Pr | H | 7-N(Pen)CO(4-Cl—Ph) |
| IV-37 | —SO$_2$NHCO—(CH$_2$)$_5$NH$_2$ | Pr | H | 7-N(Pr)CO$_2$—$^i$Bu |
| IV-38 | —SO$_2$NHCO—(CH$_2$)$_5$NH$_2$ | Pr | Me | 2-CF$_3$-phenyl |
| IV-39 | —SO$_2$NHCO—(CH$_2$)$_5$NH$_2$ | Pr | —CF$_2$CF$_3$ | 2-Cl-phenyl |

In another embodiment of the novel compounds of this invention is that of formula Ia (M is NR$^{22}$) wherein K is —N(R$^{8a}$)—C(=NR$^{22}$)—.

In a class of this embodiment:
R¹ is —COOH;

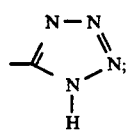

—NH—SO$_2$CF$_3$: C$_2$R$^4$; —SO$_2$NH-heteroaryl or —CH$_2$SO$_2$NH-heteroaryl wherein the heteroaryl is an unsubstituted, monosubstituted or disubstituted 5-or 6-membered aromatic ring comprising 1 to 3 heteroatoms selected from O, N and S and wherein the substituents are members selected from the group consisting of OH, SH, C$_1$-C$_4$-alkyl, C$_1$-C$_4$-alkoxy, CF$_3$, Cl, Br, F, I, NO$_2$, CO$_2$H, CO$_2$-C$_1$-C$_4$-alkyl, NH$_2$, NH(C$_1$-C$_4$-alkyl) and N(C$_1$-C$_4$-alkyl)$_2$; —SO$_2$NHCOR$^{23}$; —CH2SO$_2$NHCOR$^{23}$; —CONHSO$_2$R$^{23}$; —CH$_2$CONHSO$_2$R$^{23}$; —NHSO$_2$NHCOR$^{23}$; and —NHCONHSO$_2$R$^{23}$;

R$^{2a}$ and R$^{2b}$ are H, F, Cl, CF$_3$, C$_1$-C$_4$-alkyl or C$_1$-C$_4$-alkoxy;

R$^{3a}$ is H, F or Cl;

R$^{3b}$ is H, F, Cl, CF$_3$, C$_1$-C$_4$-alkyl, C$_5$-C$_6$-cycloalkyl, —COOCH$_3$, —COOC$_2$H$_5$, —SO$_2$CH$_3$; NH$_2$, —N(-C$_1$-C$_4$-alkyl)$_2$ or —NH—SO$_2$CH$_3$;

E is a single bond, —O— or —S—;

R$^6$ is (a) $C_1$-$C_5$-alkyl, $C_2$-$C_5$-alkenyl or $C_2$-$C_5$-alkynyl each of which can be substituted with a substituent selected from the group consisting of Cl, $CF_3$, $CCl_3$, —O—$CH_3$, —$OC_2H_5$, —S—$CH_3$, —S—$C_2H_5$, phenyl, and $C_3$-$C_5$-cycloalkyl;

(b) $C_3$-$C_5$-cycloalkyl;

(c) perfluoro-$C_1$-$C_4$-alkyl; $R^7$ and $R^{8a}$ are as defined above or together with the atoms to which they are bonded may be joined to form a pyridine ring which may be substituted with $R^{26}$ and $R^{27}$; and X is a C—C single bond.

In a more preferred class of this embodiment are those compounds wherein:
E is a single bond;
$R^{2a}$, $R^{2b}$, $R^{3a}$ and $R^{3b}$ are each H; and
X is a single bond.

Exemplifying this embodiment are the following compounds of the Formula V shown in Table 4:

Also exemplifying this embodiment are the following compounds of the Formula VI shown in Table 5:

TABLE 4

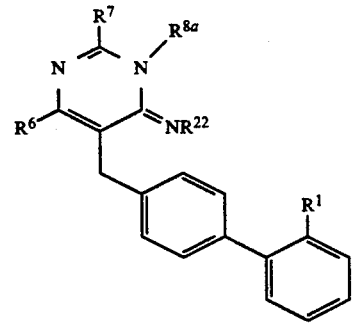

V

| Compd. No. | $R^1$ | $R^6$ | $R^7$ | $R^{8a}$ | $R^{22}$ |
|---|---|---|---|---|---|
| V-1 | tetrazol-5-yl | Bu | Me | H | —$CF_3$-phenyl |
| V-2 | tetrazol-5-yl | Pr | Me | 2-$CF_3$-phenyl | Me |
| V-3 | tetrazol-5-yl | Pr | Me | 2-Cl-phenyl | Me |
| V-4 | tetrazol-5-yl | Pr | Me | 2,6-diCl-phenyl | Me |
| V-5 | tetrazol-5-yl | Pr | —$CF_2CF_3$ | 2-$CF_3$-phenyl | Me |
| V-6 | tetrazol-5-yl | Pr | —$CF_2CF_3$ | 2-Cl-phenyl | Me |
| V-7 | tetrazol-5-yl | Pr | Me | 2-COOH-phenyl | Me |
| V-8 | tetrazol-5-yl | Pr | Me | —$CF_2CF_3$ | 2-pyridyl |
| V-9 | —$NHSO_2CF_3$ | Bu | Me | H | 2-$CF_3$-phenyl |
| V-10 | —$NHSO_2CF_3$ | Pr | Me | 2-$CF_3$-phenyl | Me |
| V-11 | —$NHSO_2CF_3$ | Pr | Me | 2-Cl-phenyl | Me |
| V-12 | —$NHSO_2CF_3$ | Pr | Me | 2,6-diCl-phenyl | Me |
| V-13 | —$NHSO_2CF_3$ | Pr | —$CF_2CF_3$ | 2-$CF_3$-phenyl | Me |
| V-14 | —$NHSO_2CF_3$ | Pr | —$CF_2CF_3$ | 2-Cl-phenyl | Me |
| V-15 | —$NHSO_2CF_3$ | Pr | Me | 2-COOH-phenyl | Me |
| V-16 | —$NHSO_2CF_3$ | Pr | Me | —$CF_2CF_3$ | 2-pyridyl |
| V-17 | —$SO_2NHCO^{cy}Pr$ | Pr | Me | 2-$CF_3$-phenyl | Me |
| V-18 | —$SO_2NHCO^{cy}Pr$ | Pr | Me | 2-Cl-phenyl | Me |
| V-19 | —$SO_2NHCO^{cy}Pr$ | Pr | Me | 2,6-diCl-phenyl | Me |
| V-20 | —$SO_2NHCO^{cy}Pr$ | Pr | —$CF_2CF_3$ | 2-$CF_3$-phenyl | Me |
| V-21 | —$SO_2NHCO^{cy}Pr$ | Pr | —$CF_2CF_3$ | 2-Cl-phenyl | Me |
| V-22 | —$SO_2NHCO^{cy}Pr$ | Pr | Me | 2-COOH-phenyl | Me |
| V-23 | —$SO_2NHCO^{cy}Pr$ | Pr | Me | —$CF_2CF_3$ | 2-pyridyl |
| V-24 | —$SO_2NHCOPh$ | Pr | Me | 2-$CF_3$-phenyl | Me |
| V-25 | —$SO_2NHCOPh$ | Pr | Me | 2-Cl-phenyl | Me |
| V-26 | —$SO_2NHCOPh$ | Pr | Me | 2,6-diCl-phenyl | Me |
| V-27 | —$SO_2NHCOPh$ | Pr | —$CF_2CF_3$ | 2-$CF_3$-phenyl | Me |
| V-28 | —$SO_2NHCOPh$ | Pr | —$CF_2CF_3$ | 2-Cl-phenyl | Me |
| V-29 | —$SO_2NHCOPh$ | Pr | Me | —$CF_2CF_3$ | Me |
| V-30 | —$SO_2NHCOPh$ | Pr | Me | 2-COOH-phenyl | Me |
| V-31 | —$SO_2NHCO$—$(CH_2)_5NH_2$ | Pr | Me | 2-$CF_3$-phenyl | Me |
| V-32 | —$SO_2NHCO$—$(CH_2)_5NH_2$ | Pr | —$CF_2CF_3$ | 2-Cl-phenyl | Me |

TABLE 5

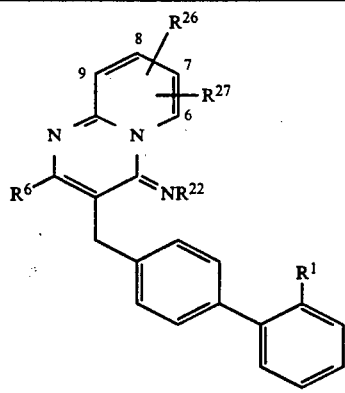

VI

| Compd. No. | R¹ | R⁶ | R²² | R²⁶ | R²⁷ |
|---|---|---|---|---|---|
| VI-1 | tetrazol-5-yl | Bu | cyPr | H | 7-Me |
| VI-2 | tetrazol-5-yl | Bu | cyPr | H | 7-iPr |
| VI-3 | tetrazol-5-yl | Pr | Me | H | 7-N(Pen)COPh |
| VI-4 | tetrazol-5-yl | Pr | Me | H | 7-N(Pen)CO(4-Cl—Ph) |
| VI-5 | tetrazol-5-yl | Pr | Me | H | 7-N(Pr)CO$_2$—iBu |
| VI-6 | tetrazol-5-yl | Pr | Me | H | 7-N(Bn)COBu |
| VI-7 | tetrazol-5-yl | Bu | cyPr | 8-Cl | 7-SO$_2$Me |
| VI-8 | tetrazol-5-yl | Bu | cyPr | H | 8-Cl |
| VI-9 | —NHSO$_2$CF$_3$ | Bu | cyPr | H | 7-Me |
| VI-10 | —NHSO$_2$CF$_3$ | Bu | cyPr | H | 7-iPr |
| VI-11 | —NHSO$_2$CF$_3$ | Pr | Me | H | 7-N(Pen)COPh |
| VI-12 | —NHSO$_2$CF$_3$ | Pr | Me | H | 7-N(Pen)CO(4-Cl—Ph) |
| VI-13 | —NHSO$_2$CF$_3$ | Pr | Me | H | 7-N(Pr)CO$_2$—iBu |
| VI-14 | —NHSO$_2$CF$_3$ | Pr | Me | H | 7-N(Bn)COBu |
| VI-15 | —NHSO$_2$CF$_3$ | Bu | cyPr | 8-Cl | 7-SO$_2$Me |
| VI-16 | —NHSO$_2$CF$_3$ | Bu | cyPr | H | 8-Cl |
| VI-17 | —SO$_2$NHCOcyPr | Bu | cyPr | H | 7-Me |
| VI-18 | —SO$_2$NHCOcyPr | Bu | cyPr | H | 7-iPr |
| VI-19 | —SO$_2$NHCOcyPr | Pr | Me | H | 7-N(Pen)COPh |
| VI-20 | —SO$_2$NHCOcyPr | Pr | Me | H | 7-N(Pen)CO(4-Cl—Ph) |
| VI-21 | —SO$_2$NHCOcyPr | Pr | Me | H | 7-N(Pr)CO$_2$—iBu |
| VI-22 | —SO$_2$NHCOcyPr | Pr | Me | H | 7-N(Bn)COBu |
| VI-23 | —SO$_2$NHCOcyPr | Bu | cyPr | 8-Cl | 7-SO$_2$Me |
| VI-24 | —SO$_2$NHCOcyPr | Bu | cyPr | H | 8-Cl |
| VI-25 | —SO$_2$NHCOPh | Bu | cyPr | H | 7-Me |
| VI-26 | —SO$_2$NHCOPh | Bu | cyPr | H | 7-iPr |
| VI-27 | —SO$_2$NHCOPh | Pr | Me | H | 7-N(Pen)COPh |
| VI-28 | —SO$_2$NHCOPh | Pr | Me | H | 7-N(Pen)CO—(4-Cl—Ph) |
| VI-29 | —SO$_2$NHCOPh | Pr | Me | H | 7-N(Pr)CO$_2$—iBu |
| VI-30 | —SO$_2$NHCOPh | Pr | Me | H | 7-N(Bn)COBu |
| VI-31 | —SO$_2$NHCOPh | Bu | cyPr | 8-Cl | 7-SO$_2$Me |
| VI-32 | —SO$_2$NHCOPh | Bu | cyPr | H | 8-Cl |
| VI-33 | —SO$_2$NHCO—(CH$_2$)$_5$NH$_2$ | Bu | cyPr | H | 7-Pr |
| VI-34 | —SO$_2$NHCO—(CH$_2$)$_5$NH$_2$ | Bu | cyPr | 8-Cl | 7-SO$_2$Me |
| VI-35 | —SO$_2$NHCO—(CH$_2$)$_5$NH$_2$ | Bu | cyPr | H | 8-Cl |
| VI-36 | —SO$_2$NHCO—(CH$_2$)$_5$NH$_2$ | Pr | Me | H | 7-N(Pen)CO(4-Cl—Ph) |
| VI-37 | —SO$_2$NHCO—(CH$_2$)$_5$NH$_2$ | Pr | Me | H | 7-N(Pr)CO$_2$—iBu |
| VI-38 | —SO$_2$NHCO—(CH$_2$)$_5$NH$_2$ | Pr | cyPr | H | 7-iPr |
| VI-39 | —SO$_2$NHCO—(CH$_2$)$_5$NH$_2$ | Pr | cyPr | H | 7-SO$_2$Me |

Several methods for preparing the compounds of this invention are illustrated in the ensuing Schemes.

Abbreviations Used in Schemes

Reagents:

| | |
|---|---|
| NBS | N-bromosuccinimide |
| AIBN | Azo(bis)isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |

Solvents:

| | |
|---|---|
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |

Others:

| | |
|---|---|
| rt | room temperature |
| TBDMS | t-butyldimethylsilyl |
| OTf | OSO$_2$CF$_3$ |
| OTs | OSO$_2$-(4-methyl)phenyl |
| OMs | OSO$_2$CH$_3$ |

| Abbreviations Used in Schemes | |
|---|---|
| Ph | phenyl |
| FAB-MS (FABMS) | Fast atom bombardment mass spectroscopy |
| NOE | Nuclear Overhauser Effect |
| SiO$_2$ | silica gel |
| trityl | triphenylmethyl |

Pyrimidinones substituted in the 2,4,5, and 6 positions may be prepared as shown in Scheme 1. The dianion of ethyl hydrogen malonate is made using two equivalents of butyllithium in THF at −78° C. It is then quenched with an acyl chloride then acidified giving the necessary β-ketoester as shown.[1] The β-ketoester is then alkylated with the appropriate sidechain using sodium hydride in DMSO (or other suitable base in a suitable solvent) to give intermediate 1. Intermediate 1 may then be treated with an appropriate R$^7$-amidine, guanidine, O-alkyl or aryl isourea, or S-alkyl or aryl isothiourea, to give the 2,5,6-trisubstituted pyrimidin-4(3H)-one 2.[2]

Pyrimidin-4(3H)-one 2 itself may be an A-II antagonist but may also be used as an intermediate for the preparation of 2,3,5,6-tetrasubstituted pyrimidin-4(3H)-ones as indicated in Scheme 2. Intermediate 2 may be deprotonated in DMF with sodium hydride (or other suitable solvent and base) and alkylated with an R$^{8a}$electrophile to afford the pyrimidin-4(3H)one 3.[3]

Scheme 3 illustrates an alternative preparation of pyrimidinone 3. An R$^7$ nitrile can be converted to an imidate then to an amidins with an R$^{8a}$amine. This can then be condensed with B-ketoester 1 to give 3. Similar procedures also exist for the preparation of isoureas, isothiuronium salts, and guanidines.[4] Other methods are also available for the introduction of substituents at the 2-position of the pyrimidine.[5]

Scheme 4 shows how pyrimidinone 2 can be converted to 4-chloropyrimidine 4, which is a useful intermediate for the preparation of other 4-substituted pyrimidines. One could also envision using triflic anhydride and a suitably hindered amine base to give the corresponding pyrimidine trillate that could be used in a similar fashion to the 4-chloropyrimidine.[6]

Scheme 5 shows how nucleophilic displacement would be achieved using an R$^{8b}$ nucleophile which could be an amine, alcohol, thiol, or carbon nucleophile with or without a Ni$^{2+}$or Pd$^0$ catalyst, to give the 2,4,5,6-tetrasubstituted pyrimidine 5.[7]

Scheme 6 provides a route to the useful intermediate β-ketonitrile 6. Cyanoacetic acid can be condensed with an R$^6$ acyl chloride to give the α-unsubstituted R$^6$ β-ketonitrile.[8] This can then be α-alkylated using NaH in DMSO (or other suitable base and solvent) and the appropriate sidechain electrophile to afford 6.

Scheme 7 shows how the S-ketonitrile 6 can be condensed with an amidine or isourea to give 4-aminopyrimidine 7. The 4-aminopyrimidines such as 7 can be converted to pyrimidin-4(3H)-ones simply by diazotizing them with nitrous acid.[9]

Scheme 8 shows an alternative pyrimidinone synthesis via an intermediate isoxazole.[10] The β-ketonitrile 6 can be converted to the 5-aminoisoxazole 8 upon treatment with hydroxylamine. Acylation with an R$^7$ acyl halide gives intermediate isoxazole 9 which upon reduction and heating gives pyrimidinone 2.

Pyridopyrimidinones such as 10 can be obtained by condensing variously substituted 2-aminopyridines with B-ketoesters 1 as shown in Scheme 9.[11]

Scheme 10 illustrates a preparation of a 4-carboxy or 4-carboalkoxy pyrimidine. Ethyl hydrogen malonate can be doubly deprotonated using two equivalents of butyllithium. The dianion can then be used as a nucleophile on which to add the electrophile sidechain to give ethyl ester 11. The ester can then be deprotonated and be added to diethyl oxalate to give the diethyl oxalacetate derivative 12.[12] Condensation of this material with an R$^7$ amidine or isourea would give the 6-carbo-ethoxypyrimidin-4(3H)-one 13.[13] Conversion of this material to the 4-chloro (or 4-trifluoromethane- sulfonato) derivative followed by nucleophilic displacement by an R6-E: nucleophile such as an amine, alkoxide, or thiol, would give the 2,5,6-trisubstituted-4-carboethoxypyrimidine 14. Hydrolysis of the ester would give the corresponding 4-carboxypyrimidine.

Conversion of the 4-carboxypyrimidine to the 4-acetyl derivative followed by peracid oxidation and hydrolysis would give pyrimidinone 15 as illustrated in Scheme 11. Scheme 12 shows how the 2,3,5,6-tetrasubstituted pyrimidin-4(3H)-one 16 could be prepared from pyrimidinone 15. Scheme 13 shows how the 2,4,5,6-tetrasubstituted pyrimidine 17 can be prepared from intermediate 15 with the R$^{8b}$ nucleophile as described above.[14] Alternatively, one could use triflic anhydride and hindered amine base in place of POCl$_3$.

Scheme 14 illustrates how the pyrimidine ring system can be built onto what would become the 5-sidechain. Conversion of the bromide 18 to a Grignard reagent, organo-zinc reagent, organo-lithium reagent, or other related organo-metal reagent followed by addition of diethyl oxalate would give the pyruvate derivative 19. Addition of methoxy- or ethoxymethylenetriphenylphosphorane or related reagent would give the ethyl β-ethoxyacrylate derivative 20- Condensation of this material with an R$^7$-amidine or isourea would provide pyrimidinone 21. Conversion of the 4-hydroxy function to the methoxy followed by addition of a Grignard reagent or alkyllithium and oxidation with dichlorodicyanoquinone would afford the 2,5,6-trisubstituted-4-methoxy-pyrimidin-4(3H)-one 23. Conversion of the methoxy back to a hydroxy then provides pyrimidinone 2.

Scheme 15 describes the preparation of 4-methoxy-5-bromopyrimidines 25 that may either be converted into nucleophiles and added to the electrophilic sidechain as shown in Scheme 16 or used as electrophiles as illustrated in Scheme 17. Condensation of β-ethoxyacrylate with R$^7$-amidine or isourea would provide pyrimidinone 24. Conversion of this material to the 4-methoxy-5-bromopyrimidine 25 is straight forward as shown.

In Scheme 16 the 5-bromopyrimidine is converted to a Grignard, organolithium, or related reagent then added to the electrophilic sidechain (a catalyst or stoichiometric reagent such as CuCN may be added to enhance nucleophilicity or selectivity if necessary) to give pyrimidine 22 which may be used as illustrated previously.

Scheme 17 provides a route to the same intermediate 22 by conversion of the bromide 18 to the organo-metal reagent followed by addition to the electrophilic 5-bromopyrimidine 25.

Scheme 21 illustrates one specific method used to prepare two of the more preferred compounds in Table 1. Scheme 22 illustrates another specific method used to prepare a preferred compound in Table 3.

IDENTIFICATION OF REFERENCES CITED IN SCHEMES

W. Wierenga, H. I. Skulnick, *Org. Syn.* (1982) 61 5.

D.J. Brown, The Pyrimidines, (1962), J. Wiley & Sons, pp. 48–51.

S. Hirokami, T. Takahashi, K. Kurosawa, M. Nagata, *J. Org. Chem.* (1985) 50 166. T. Takahashi, S. Hirokami, M. Nagata, T. Yamazaki, *J. Chem. Soc., Perkin Trans. I* (1988) 2653.

S. S. Ahmad, S. I. Haidea, I. Fatima, *Syn. Comm.* (1987) 17 1861.

G. D. Dares Jr., F. Baiocchi, R. K. Robins, C. C. Cheng, *J. Org. Chem.* (1961) 26 2756.

J. R. Marshall, J. Walker, *J. Chem. Soc.* (1951) 1004.

T. Sakamoto, H. Yoshizawa, H. Yamanaka, *Chem. Pharm. Bull.* (1984) 32 2005,

J. C. Krauss, T. L. Cupps, D. S. Wise, L. B. Townsend, *Synthesis* (1983) 308.

D. J. Brown, The Pyrimidines, (1962), J. Wiley & Sons, p. 333.

G. Shaw, G. Sugowdz, *J. Chem. Soc.* (1954) 665. Y. Honma, Y. Sekine, T. Hashiyama, M. Takeda, Y. Ono, K. Tsuzurahara, *Chem. Pharm. Bull.* (1982) 30 4314.

M. Shut, S. S. Israelstam, *J. Org. Chem.* (1968) 33 3015. F. Fulop, I. Hermecz, Z. Meszaros, G. Dombi, G. Bernath, *J. Het. Chem.* (1979) 16 457. P. L. Ferrarini, C. Mori, O. Livi, G. Biagi, A. M. Marini, *J. Het. Chem.* (1983) 20 1053. H. Antaki, V. Petrow, *J. Chem. Soc.* (1951) 551.

M. W. Goldberg, F. Hunziker, J. R. Billeter, H. R. Rosenberg, *Helv. Chim. Acta.* (1947) 30 200.

W. K. Hagmann, F. Z. Basha, M. Hashimoto, R. B. Frye, S. Kojo, S. M. Hecht, *J. Org. Chem.* (1981) 46 1413.

T. A. Riley, W. J. Hennen, N. K. Dalley, B. E. Wilson, R. K. Robins, S. B. Larson, *J, Het. Chem.* (1987) 24 955.

Y. Muraoka, T. Takita, K. Maeda, H. Umezawa, *J. Antibiotics* (1970) 23 253.

M. Otsuka, S. Kobayashi, M. Ohno, Y. Umezawa, H. Morishima, H. Umezawa, *Chem. Pharm. Bull.* (1985) 33 515.

G. D. Davies, Jr., R. Baiocchi, R. K. Robins, C. C. Cheng, *J. Org. Chem.* (1961) 26 2755.

E. Ochiai, H. Yamanaka, *Chem. Pharm. Bull.* (1955) 3 173.

SCHEME 1

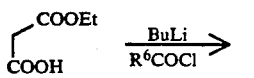

SCHEME 1

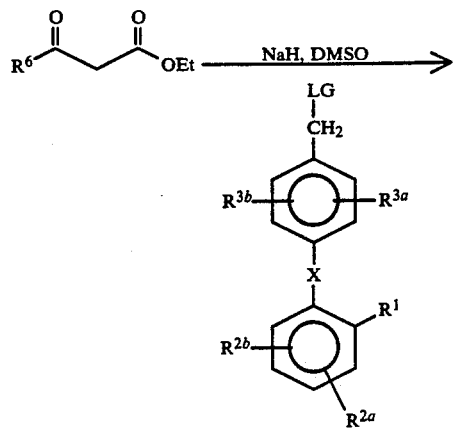

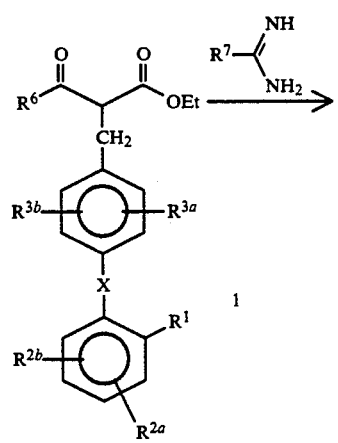

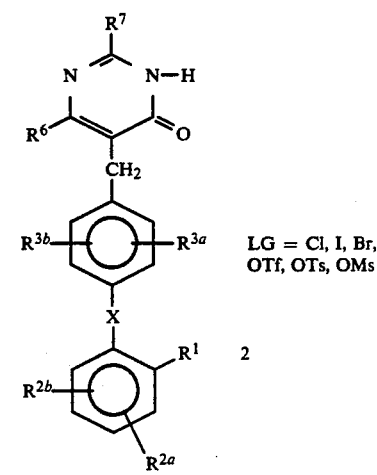

LG = Cl, I, Br, OTf, OTs, OMs

SCHEME 2
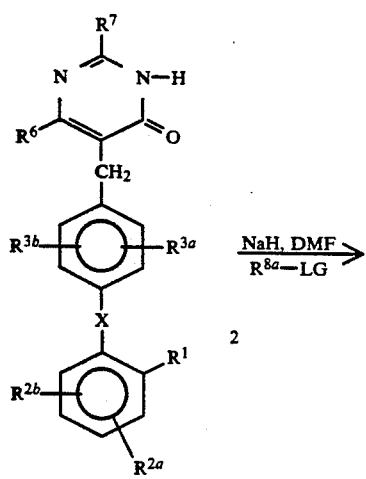
SCHEME 3
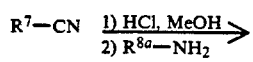
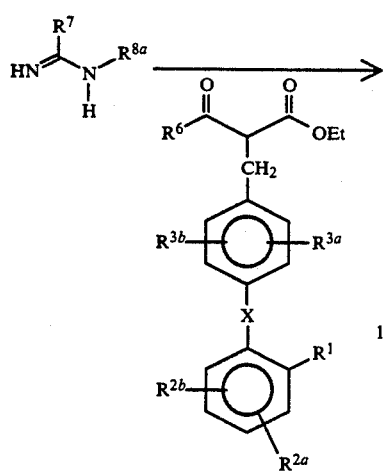
-continued
SCHEME 3
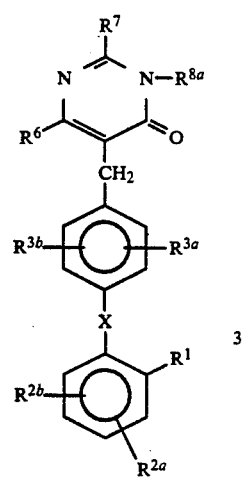
SCHEME 4
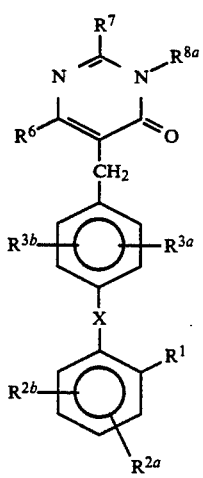
SCHEME 5
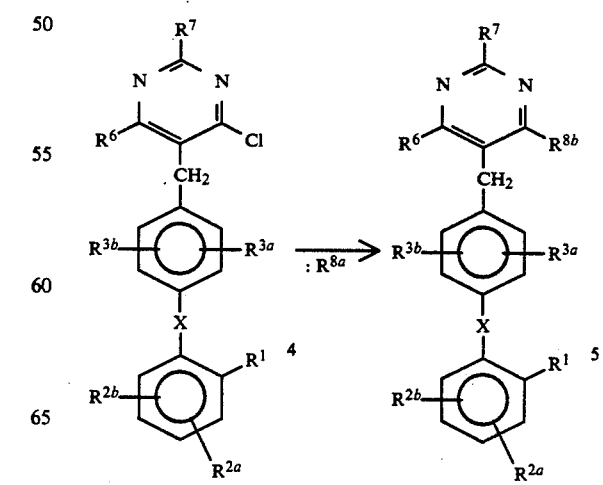

SCHEME 6
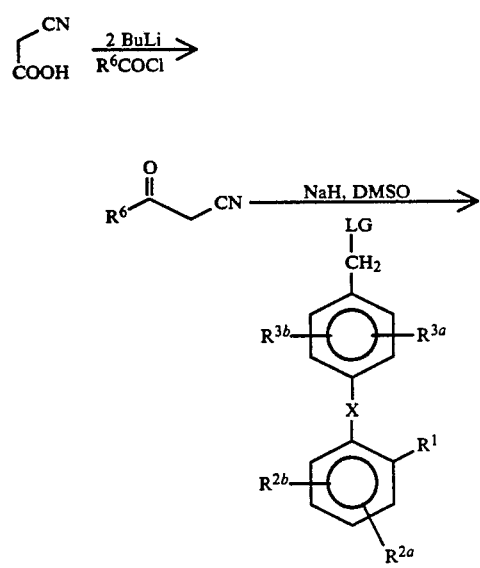
SCHEME 7
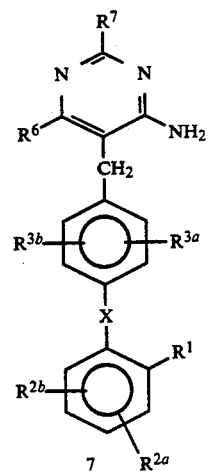
SCHEME 7
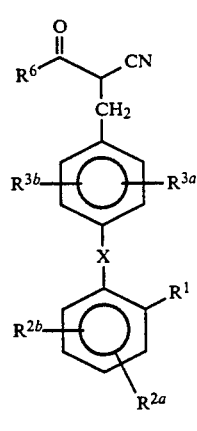
SCHEME 8
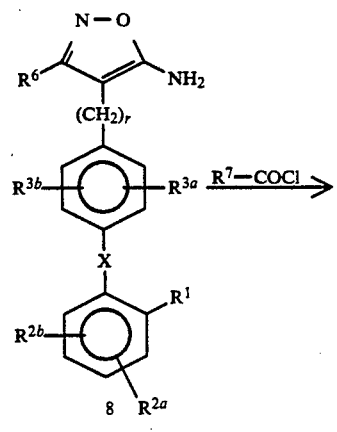
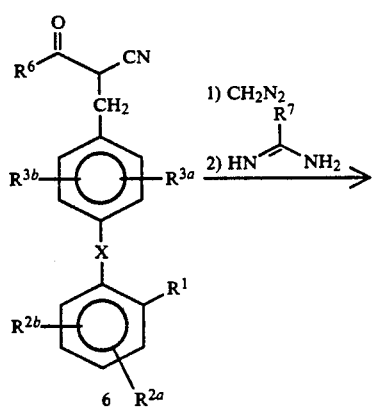

-continued
SCHEME 8
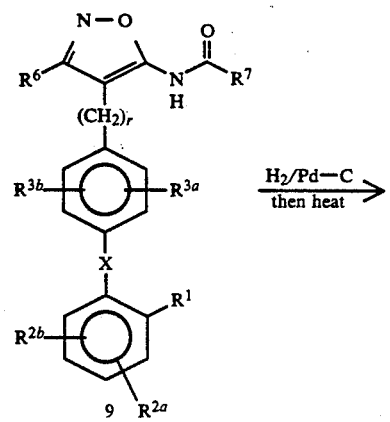
9
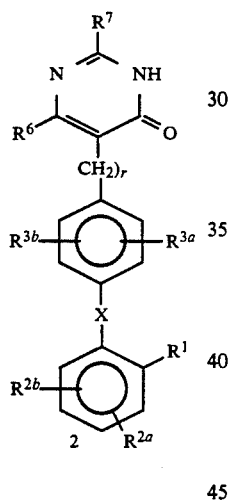
2
-continued
SCHEME 9
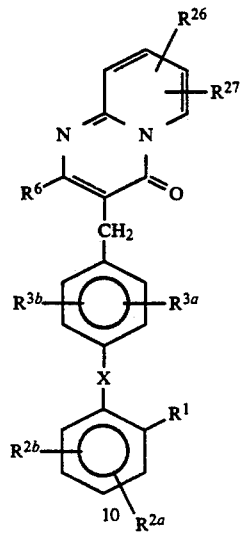
10
SCHEME 10
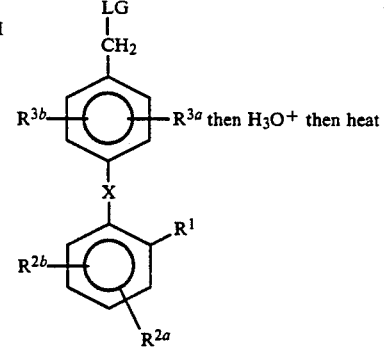
SCHEME 9
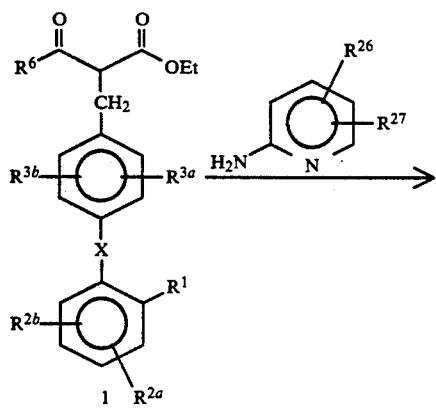
1
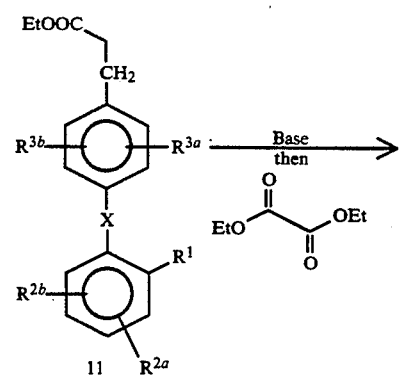
11

SCHEME 10
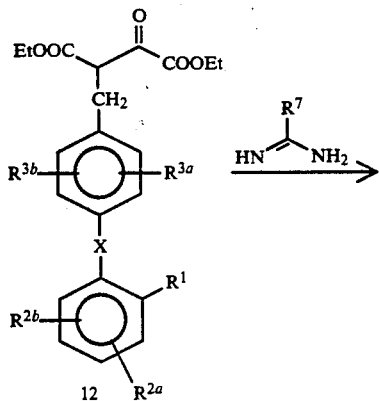
SCHEME 11
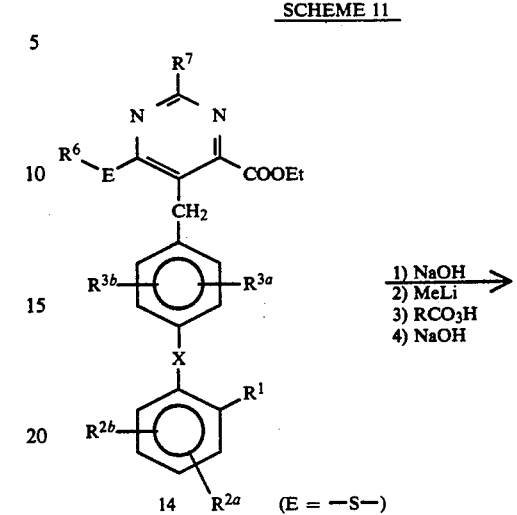
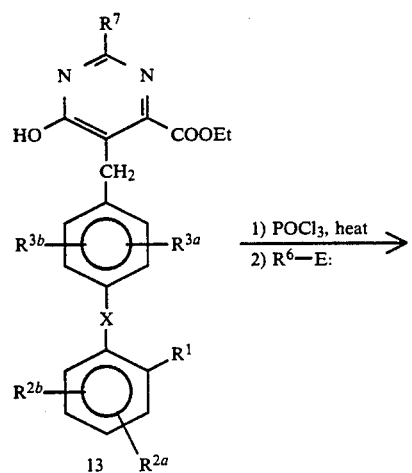
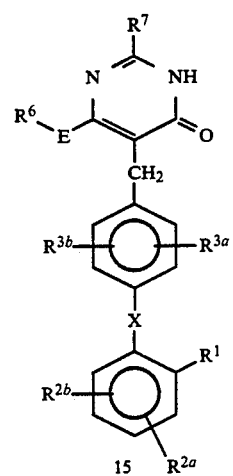
SCHEME 12
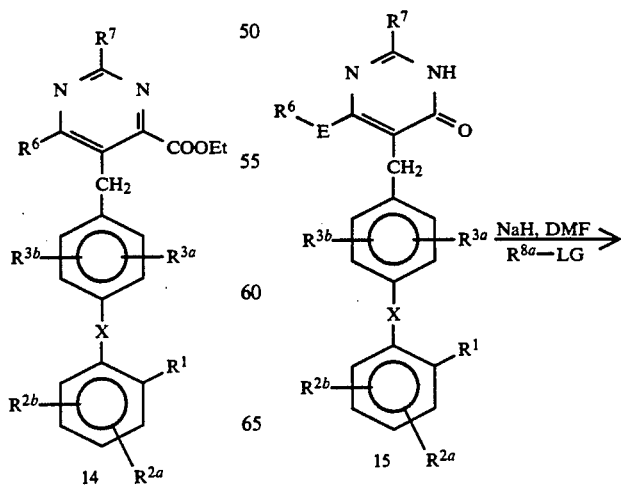

SCHEME 12
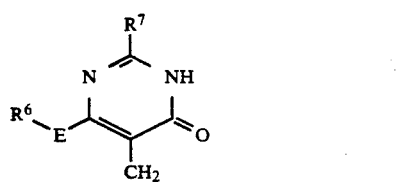
16
SCHEME 13
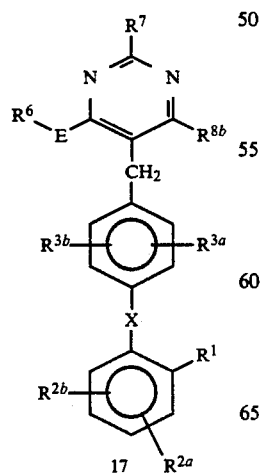
15
↓ 1) POCl₃
2): R⁸ᵇ
17
SCHEME 14
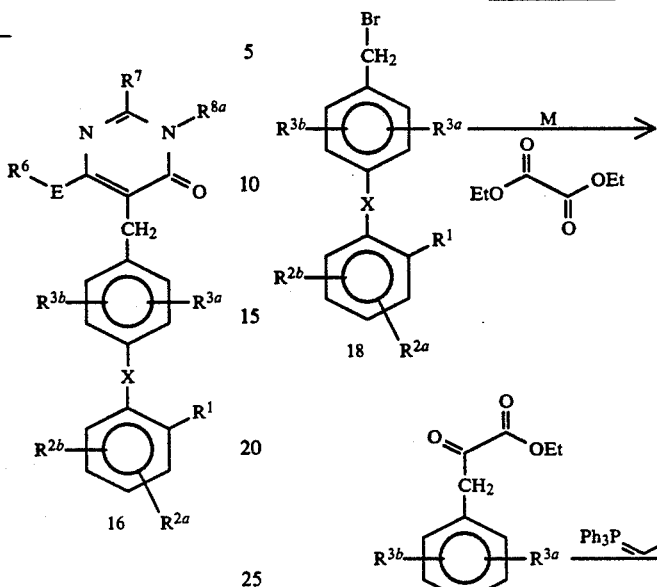
18
↓ M
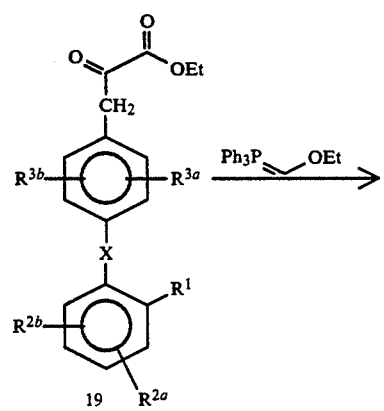
19
↓ Ph₃P=CHOEt
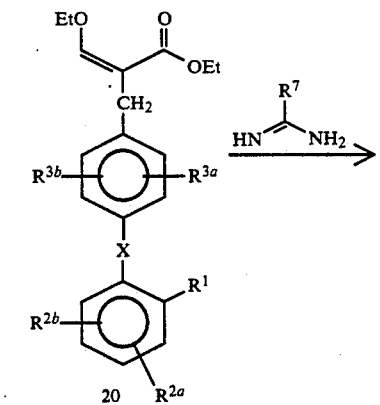
20
↓ R⁷-C(=NH)NH₂
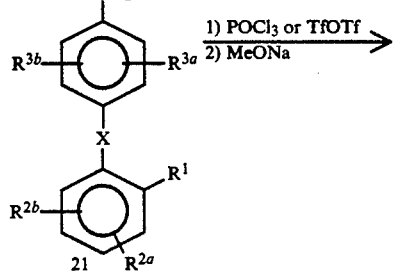
21
↓ 1) POCl₃ or TfOTf
2) MeONa 5,324,729
35
-continued
SCHEME 14
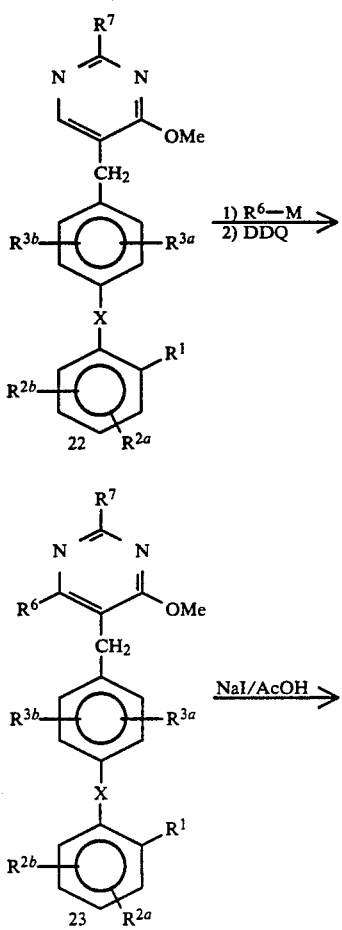
36
-continued
SCHEME 15
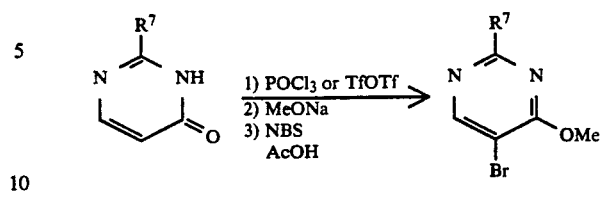
SCHEME 16
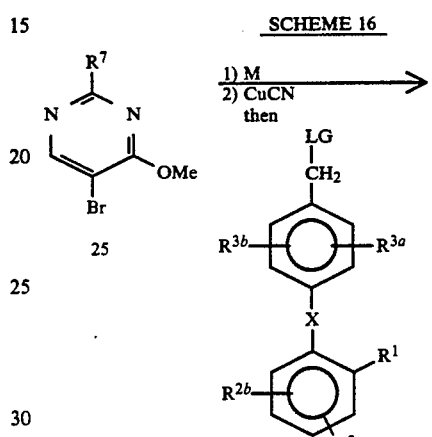
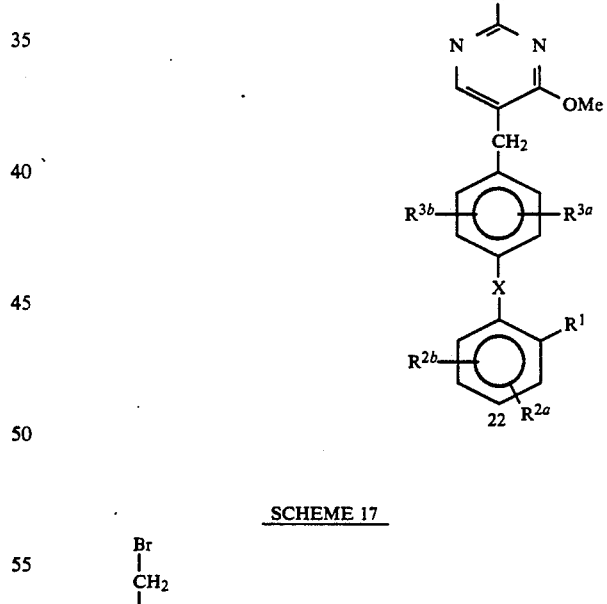
SCHEME 15
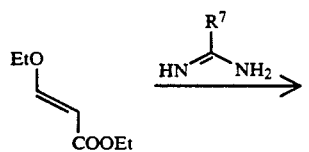
SCHEME 17
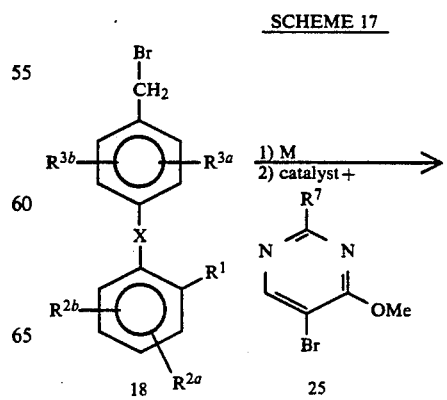

SCHEME 17 -continued

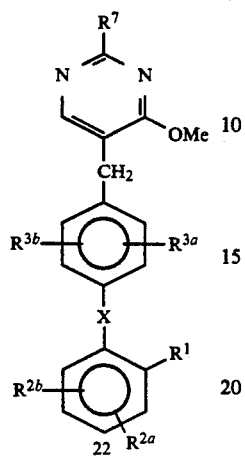

Where condensations of N—C—N group (amidines, isoureas, isothiuronium salts, etc.) with the C—C—C group (generally the β-keto esters) fail because of initial addition of N—C—N group to the ester rather than the keto group, the β-keto esters may be converted to β-acetoxy, β-ethoxy, β-enol phosphate, β-enol triflate, or similar β-leaving group α, β-unsaturated esters. [E. Piers, et al, *Tet.Lett.*, 25, 3155 (1984); M. Alderdice, etal, *Org. Syn*, 62, 14 (1984)]Such a reaction is illustrated in Scheme 18. The N—C—N group may then be condensed with the C—C—C group to give the expected pyrimidinone or pyridopyrimidine.

SCHEME 18

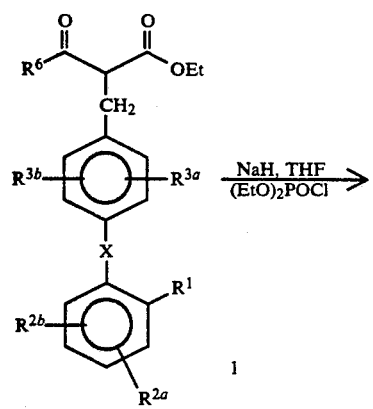

SCHEME 18 -continued

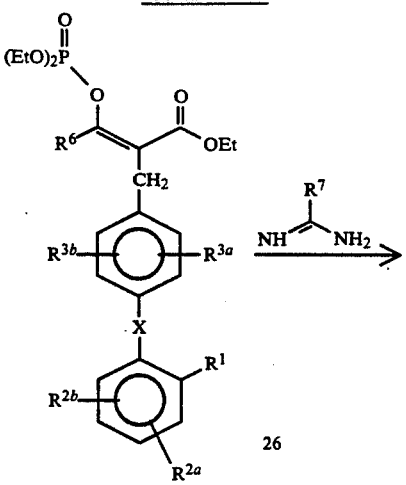

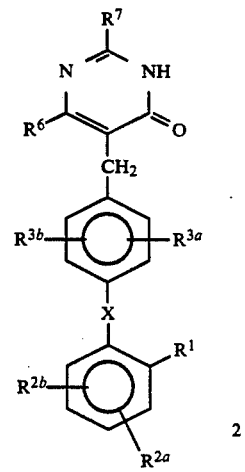

Scheme 19 provides a route for the preparation of acyl sulfonamides 27, The carboxylic acid can be activated by conversion to the acid chloride by various methods including treatment with refluxing thionyl chloride or preferably with oxalyl chloride and a catalytic amount of DHF at low temperature,[15] Activation by conversion to the acyl imidazole can be achieved upon treatment of acid 26 with carbonyldiimidazole, N,N-Diphenylcarbamoyl anhydride intermediates may be prepared as activated carbonyls,[16] Treatment of the activated carbonyls with alkali metal salts of alkyl or aryl sulfonamides or with the sulfonamide and DBU will give the expected acyl sulfonamide 27,[17]

A. W. Burgstahler, L. O. Weigel, C. G. Shaefer, *Synthesis* (1976) 767.
F. J. Brown, et al, European Patent Application EP 199543
K. L. Shepard, W. Halczenko, *J. Het. Chem.* (1979) 16 321.
J. T. Drummond, G. Johnson, *Tet. Lett.* (1988) 29 1653.
T. R. Bailey, *Tet. Lett.* (1986) 27 4407.
I. P. Beletskaya, *J. Organometallic Chem.* (1983) 250 551.

Scheme 20 provides a route to the isomeric acyl sulfonamides 33, The commercially available bromobenzenesulfonyl chloride 28may be converted to the corresponding sulfonamide upon treatment with ammonia or ammonium carbonate, Protection with the triphenylmethyl group gives sulfonamide 29. Palladium catalyzed cross-coupling gives the biaryl 30,[18] Treatment of this material with N-bromosuccinimtde and catalytic AIBN in refluxing CCl4 will give the alkylating agent 31, The bromide 31 may now be used as the alkylating agent shown in previous schemes to give intermediate 32. Deprotection and acylation will give the acyl sulfonamide 33.
SCHEME 19
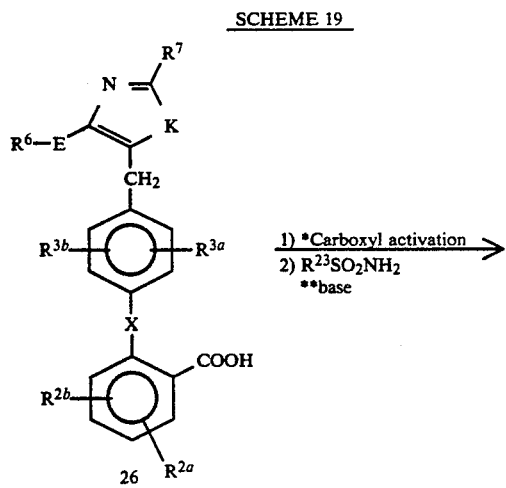
*a. SOCl₂, reflux
b. (COCl)₂, DMF, −20° C.
c. N (N,N-Diphenylcarbamoyl) pyridinium chloride/ aqueous. NaOH
d. carbonyl diimidazole
**base can be NaH, KH, DBU
SCHEME 20
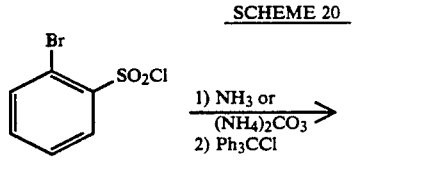
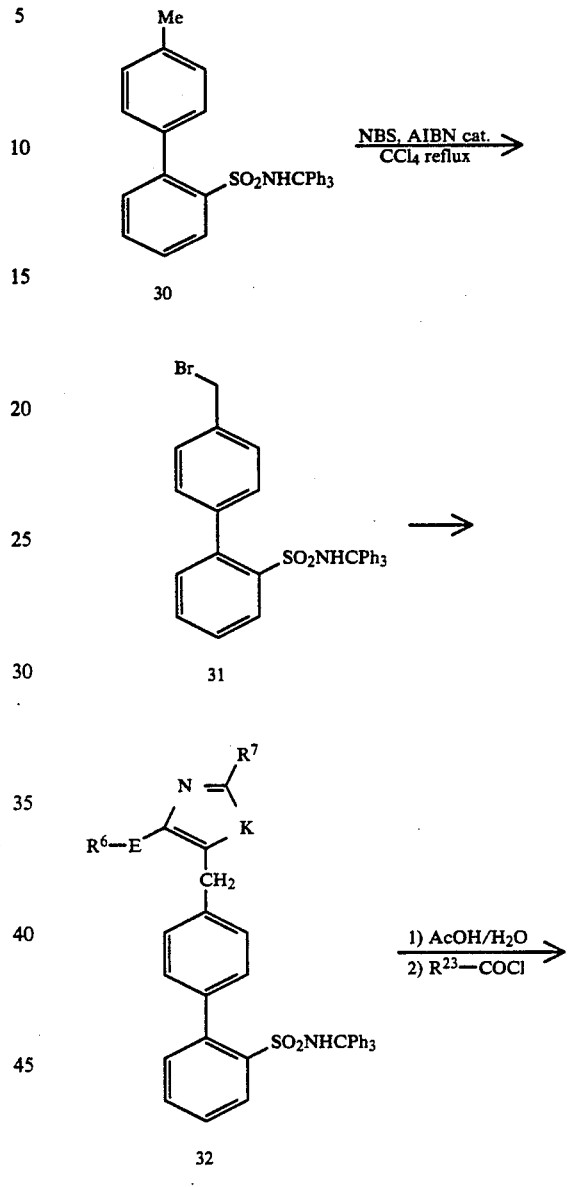

41
42
SCHEME 21
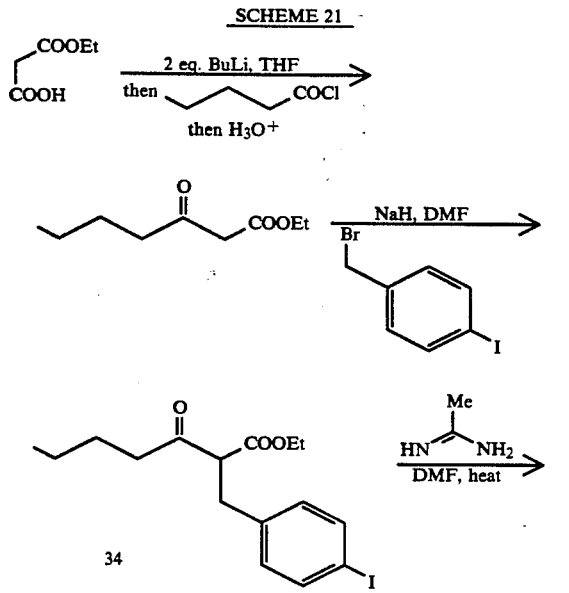
-continued
SCHEME 21
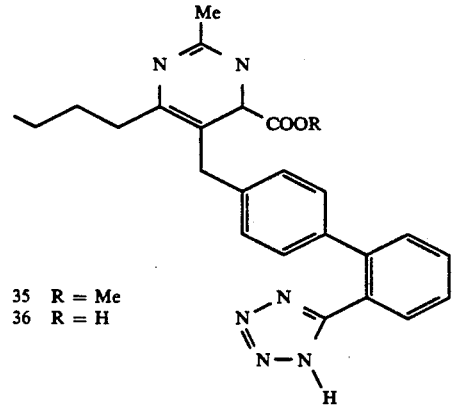
35 R = Me
36 R = H
SCHEME 22
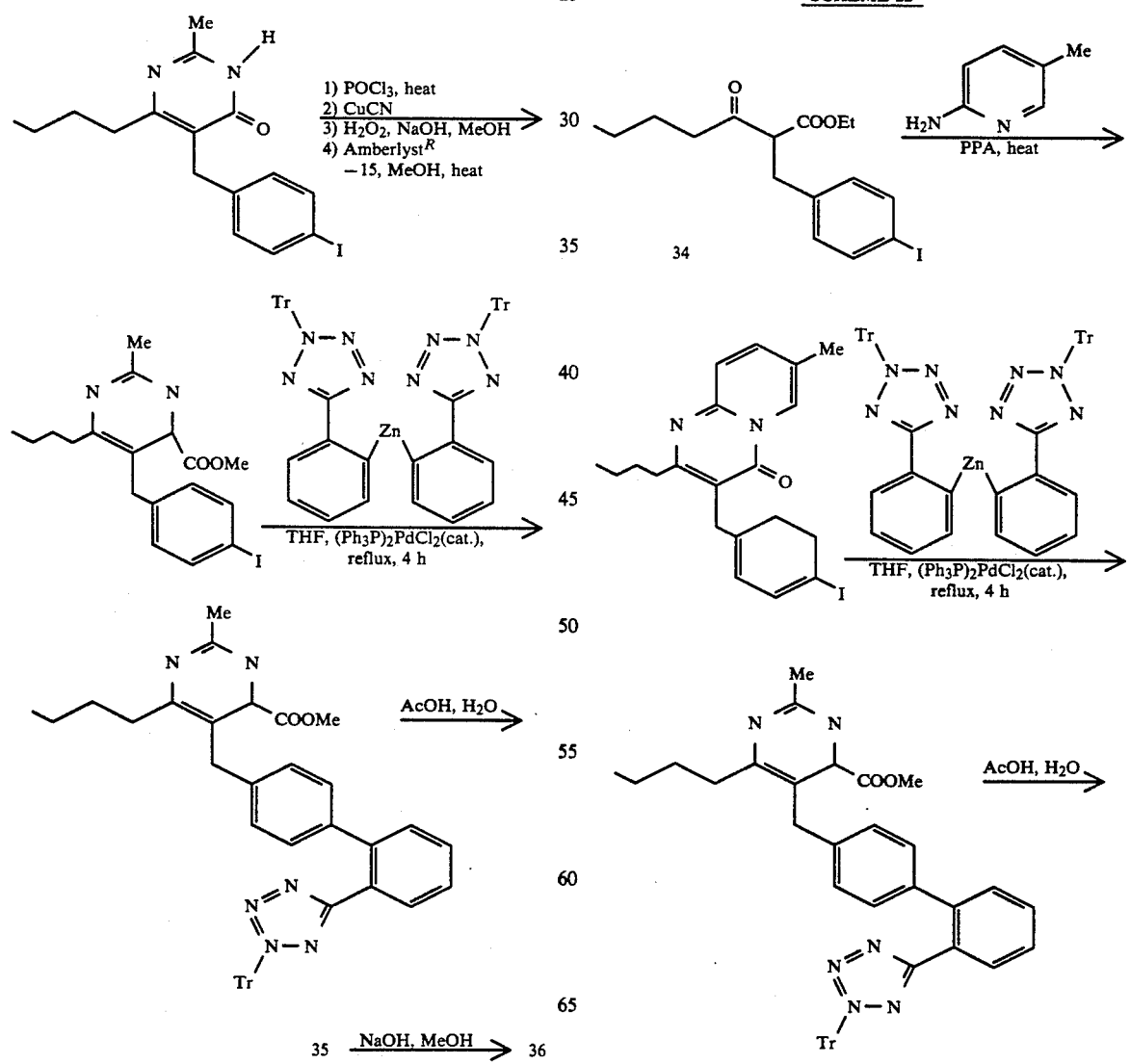
35 →(NaOH, MeOH)→ 36

-continued
SCHEME 22

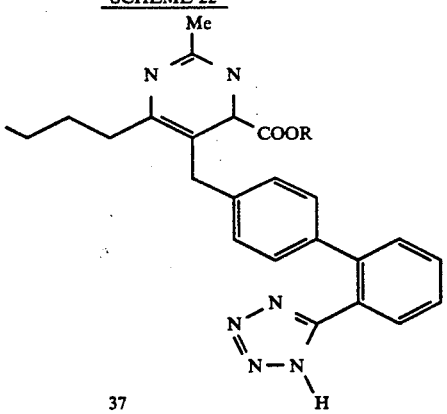

37

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluensulfonic, maleic, fumaric, camphorsulfonic. The non-toxic, physiologically acceptable salts are preferred, although other salts are also useful, e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Antiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml), homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin, and the suspension was used for 100 assay tubes. Samples tested for screening were done in duplicate. To the membrane preparation (0.25 ml) there was added $^{125}$I-Sar$^1$Ile$_8$-angiotensin II [obtained from New England Nuclear] (10 μl; 20,000 cpm) with or without the test sample, and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist, which gives 50 % displacement of the total specifically bound $^{125}$I-Sar$^1$Ile$^8$-angiotensin II , was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds generally duplicates of tubes are used). To the membrane preparation (0.5 ml) there was added 3H-angiotensin II (50 mM) (10 μl), with or without the test sample, and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist, which gives 50% displacement of the total specifically bound $^3$H-angiotensin II, was presented as a measure of the efficacy of such compounds as AII antagonists.

The potential antihypertensive effects of the compounds described in the present invention may be evaluated using the methodology described below:

Male Charles River Sprague-Dawley rats (300–3.75 gm) were anesthetized with methohexital (Brevital; 50 mg/kg j.p.). The trachea was cannulated with PE 205 tubing. A stainless steel pithing rod (1.5 nun thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received unput from a rectal temperature probe. Attopine ( 1 mg/kg i.v.) was then administered and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and were found to exhibit an activity of at least $IC_{50} < 50$ μM, thereby demonstrating and confirming the utility of the compounds of the invention as effective AII antagonists.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, sclerederma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient, depending upon the nature and severity of disease, the patient's weight, special diets then being followed by a patient, concurrent medication and other factors, which those skilled in the art will recognize the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other anti-hypertensives such as diuretics, angiotensin converting enzyme inhibitors, calcium channel blockers or β-blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, resetpine, sodium nitroprusside, spironolactone, timolol maleate, thrichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonist of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15÷200 mg), amiloride (5-20 mg), furosemide (5-80 mg), propranolol (20-480 mg), timolol maleate (5-60 mg), methyldopa (65-2000 mg), felodipine (5-60 mg), nifedipine 5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compounds or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc:, or a synthetic faffy vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-300 Fourier transform spectrometer or on a Bruker 250 MHz spectrometer. Chemical shifts are reported as (parts per million) downfield from tetramethylsilane. Mass spectra were obtained from the Merck and Co. mass spectral facility in Rahway, N.J. Analytical TLC was conducted on E. Merck precoated silica plates (0.25 mm in glass, Kieselgel 60 $F_{254}$) with UV visualization. All chromatography was conducted on E. Merck silica gel. All reactions were carried out under an atmosphere of dry nitrogen under standard conditions for those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tactine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

PREPARATION OF INTERMEDIATES

2-t-BUTOXYCARBONYL-4'-METHYLBIPHENYL,

To a solution of p-bromotoluene (30g) in dry ether (150 ml) at −78° C., a solution of t-BuLi in pentane (1.7M) (210 ml) was added slowly over a period of 1.5 hr using a dropping funnel. The bath was then removed and the mixture was stirred at room temperature for an additional 2 hours. The content of the flask was then added slowly (using a cannula) at room temperature to a premixed solution of $ZnCl_2$ in ether (1M, 180 ml) and dry THF (360 ml). The mixture was stirred for 2 hr at that temperature and then the slurry was added (using a cannula) to a solution of 2-t-butoxycarbonyl iodobenzene (35.6 g) and $NiCl_2(Ph_3P)_2$ (2.1 g) in dry THF (360 ml). The mixture, after stirring at room temperature overnight (18 hr), was poured slowly under stirring into ice-cold 0.5N HCl (1500 ml). The organic layer was separated, and the aqueous phase was extracted with ether (3×300 ml). The combined organic layer was washed with water, brine and then dried over $MgSO_4$. Removal of the solvent gave the crude product as an oil (32 g). The material was purified on a silica-gel flash column using ethyl acetate-hexane (1:12) to give the titled compound as an oil (24 g, 76%). $^1$H NMR ($CDCl_3$): δ1.24 (s,9H) 2.42 (s,3H), 7.2–7.8 (m 8H); FAB-MS: m/e 269(M+H)

4-BROMOMETHYL-2'-t-BUTOXYCARBONYL-BIPHENYL

To a solution of 2-t-butoxycarbonyl-4'-methylbiphenyl (25.3 g, 95 mmol) in $CCl_4$ (200 ml) were added freshly opened N-bromosuccinimide <17.6 g, 0.099 mole) and dibenzoyl peroxide (2.28 g, 0.0094 moles). The mixture was refluxed for 4 hours, cooled to room temperature and filtered. The filtrate was washed with sat. $NaHSO_3$ (1×50 ml), sat. $NaHCO_3$ (1×50 ml), water (1×50 ml), sat. NaCl (1×50 ml) and dried over $MgSO_4$. The solution was filtered and concentrated in vacuo. The residue was dissolved in 100 ml of hot hexane. Crystallization gradually took place as the solution cooled. The flask was finally cooled to −20° C. and the precipitate recovered by filtration. The solid was washed with ice cold hexanes and dried in vacuo to give 27 g (88%) of a white solid. $^1$H-NMR ($CDCl_3$):1.23 (s, 9H), 4.53 (s, 2H), 7.2–7.5 (m, 7H), 7.68 (d, 1H).

2-CYANO-4'-METHYLBIPHENYL

To a solution of p-bromotoluene (30 g) in dry ether (150 ml) at −78° C., a solution of t-BuLi in pentane (1.7M)<210 ml) was added slowly over a period of 1.5 hr, using a dropping funnel. The bath was then removed and the mixture was stirred at room temperature for an additional 2 hr. The contents of the flask was then added slowly (using a cannula) at room temperature to a premixed solution of $ZnCl_2$ in ether (1M) (180 ml) and dry THF (360 ml). The mixture was stirred for 2h at that temperature and then the slurry was added (using a cannula) to a solution of 2-bromobenzonitrile (21.3 g) and $NiCl_2(Ph_3P)_2$(2.1 g) in dry THF (300 ml). The mixture, after stirring at room temperature overnight (18h), was poured slowly under stirring into ice-cold 1N HCl (1500 ml). The organic layer was separated, and the aqueous phase was extracted with ether (3×300 ml). The combined organic layer was washed with water, brine and then dried over $MgSO_4$. Removal of the solvent gave the crude product as a semisolid mass (34 g). The material was purified on a silica-gel flash column using ethyl acetate-hexane (1:12) to give the desired nitrile as a low-melting solid (28 g, 88%). $^1$H NMR ($CDCl_3$): 2.42 (s, 3H), 7.2–7.8 (m, 8H); FAB-MS: m/e 194 (M++1).

TRIMETHYLSTANNYL AZIDE

To a concentrated solution of $NaN_3$ (1.2 kg, 18.5 moles) in water (3L), a solution of trimethyltin chloride (600 g, 3 moles) in dioxane (400 ml) was added in three portions under vigorous stirring. A precipitate formed instantaneously. The mixture, after stirring overnight at room temperature, was filtered. The residue was washed with water and dried under suction and then in vacuo over $P_2O_5$. Yield 541 g (88%), mp 120°–122° C.

5-[2-(4'-METHYLBIPHENYL)]TETRAZOLE

To a solution of 2-cyano-4'-methylbiphenyl (390 g, 2.02 moles) in toluene (2.3L) was added trimethyltin azide (525 g, 2.55 moles) at r.t. The mixture was refluxed for 24 h, cooled to r.t., filtered, washed with toluene and sucked dry in a funnel. The precipitate was resuspended in toluene (3.5 L) and THF (250 mL) was added. Anhydrous HCl was bubbled in at a moderate rate at r.t. to give a clear solution (45 min). Addition of HCl gas was continued for another 20 min. with stirring whereupon a white precipitate formed. The reaction mixture was stirred over night. The solid product was filtered, washed with toluene followed with ether and then dried under vacuum. This produced 250 g (53% yield of the tetrarole. m.p. 152°–154° C.; $^1$H-NMR ($CDCl_3$):2.40 (s, 3H), 7.19 (dd, 1H), 7.55 (m, 2H), 8.25 (dd, 1H).

N-TRIPHENYLMETHYL-5-[2-(4'-METHYLBIPHENYL)]TETRAZOLE

To a cloudy solution of 5-[2-(4'-methylbiphenyl)]tetrazole (250 g (1.06 mole) in $CH_2Cl_2$ (4L) was added triphenylmethylchloride (310 g 1.11 mole) at r.t. The reaction mixture was stirred and triethylamine (190 mL, 138 g, 1.36 mole) was added portionwise. After addition, the mixture was stirred at reflux for 90 min. The solution was cooled to r.t., washed with water (2×1L) and dried over $MgSO_4$, filtered through a silica gel plug and concentrated on the rotovap to a solid. This was crystallized from toluene to give the product as an off-white solid (425 g, 84%); m.p. 166°–168 ° C.; $^1$H-NMR ($CDCl_3$): 2.28 (s, 3H), 6.9–7.05 (m, 10H), 7.2–7.5 (m, 12H), 7.9 (dd, 1H).

N-TRIPHENYLMETHYL-5-[2-(4'-BROMOME-THYLBIPHENYL)] TETRAZOLE

To a solution of N-triphenylmethyl-5-[2-(4'-methylbiphenyl)] tetrazole (425 g, 0.89 moles) in CCl$_4$ (4.0 L) were added N-bromsuccinimide (159 g, 0.89 mole) and dibenzoyl peroxide (22 g, 0.089 moles). The mixture was refluxed for 2 hours, cooled to room temperature and filtered. The filtrate was concentrated in vacuo to give a thick oil. The addition of ether (2.0L) to this oil resulted in a clear solution. Crystallization, followed by filtration, gave a white solid (367 g, 74%). m.p. 137°-139.5° C.; $^1$H-NMR (CDCl$_3$): 4.38 (s, 2H), 6.9–8.0 (m, 23H).

ETHYL 3-OXOHEPTANOATE

A two liter, three neck, round bottom flask equipped with a mechanical stirrer was charged with 50 g ethyl hydrogen malonate, 875 mL dry THF, and a few milligrams of 1,10-phenanthroline as indicator, under dry nitrogen. The stirred mixture was cooled to −78° C. To this was added 308 mL 2.5M n-butyllithium in hexanes over 30 minutes until a brown color persisted several minutes. The mixture was warmed to 0° C. for ~30 minutes then was cooled to −78° C. again. To this was added 22.5 mL valeroyl chloride in 25 mL THF over 15 minutes. The mixture was then warmed to room temperature, stirred 15 minutes, and acidified with ~150 mL 5% HCl. The mixture was extracted 3 times with ether. The combined organic material was washed twice with saturated NaHCO$_3$ solution and twice with brine, dried over Na$_2$SO$_4$, stripped of solvent in vacuo, and distilled at ~15 Torr with the title compound distilling at 80°-83° C. The title compound was isolated as a clear oil, 21.4 g, 66% yield. R$_f$ 0.30 in 7% EtOAc/hexane, visualized by UV and ninhydrin stain; $^1$H-NMR (250MHz, CDCl$_3$): δ 4.19 (q, 2H), 3.44 (s, 2H), 2.54 (3 line m, 2H), 1.59 (m, 2H), 1.30 (m, 2H), 1.28 (t, 3H), 0.90 (t, 3H).

3-OXOHEPTANENITRILE

To a mechanically stirred solution of 14.3 g MgSO$_4$-dried cyanoacetic acid and ~100 mg 1,10-phenanthroline in 500 mL THF at −78° C. was added 60 mL 2.5M n-butyllithium in hexanes (~one half of the total). The indicator color persisted at this point. The solution was warmed to −5° to +5° C. after which the indicator color disappeared. Another 55 mL 2.5M n-butyllithium in hexanes was added until the indicator color again persisted. The mixture was cooled to −78° C. then 10.0 mL valeroyl chloride in 10 mL THF was added over 3 minutes. After 10 minutes the now yellow solution was allowed to warm to room temperature and stir for 1 hour. The mixture was poured into a solution of 50 mL concentrated HCl in 300 mL water. The mixture was extracted 3 times with ether. The combined organic material was washed twice with saturated NaHCO$_3$ solution then once with brine. The washes were back extracted with ether and the back extracts were washed with brine. The back extracts were combined with the other organic material and then were dried over MgSO$_4$. The organic material was stripped of solvent in vacuo then was distilled at ~1 Torr with the title compound distilling at 87°-91° C. The title compound was isolated as a clear oil, 6.32 g, 60% yield. To this material there was added 1% by weight BHT to prevent polymerization. The material was also kept refrigerated at 0° C. under nitrogen. R$_f$ 0.18 in 20% EtOAc/hexane, visualized by ninhydrin stain; $^1$H-NMR (300 MHz, CDCl$_3$): δ 3.46 (s, 2H), 2.62 (3 line m, 2H), 1.61 (m, 2H), 1.35 (m, 2H), 0.92 (t, J=7.3Hz, 3H); $^{13}$C-NMR (75.4 MHz, CDCl$_3$): δ 197.6, 113.8, 41.9, 31.9, 25.3, 22.0, 13.7.

ETHYL 2-[(2'-(N-TRIPHENYLMETHYL-TETRAZOL-5-YL)BIPHEN-4-YL)METHYL]-3-OXOHEPTANOATE

To a solution of 370 mg ethyl 3-oxoheptanoate in 10 mL DMSO was added 86 mg 60% NaH in oil. After two minutes 600 mg N-triphenylmethyl-5-[2-(4'-bromomethylbiphenyl)]tetrazole was added all at once to the solution. After 20 minutes the solution was poured into brine and extracted 3 times with ether. The organic material was dried over MgSO$_4$, stripped of solvent in vacuo, and MPLC'd in 10% EtOAc/hexane. The title compound was isolated as a white foam. R$_f$ 0.30 in 20% EtOAc/hexane, visualized by UV and ammonium molybdate/ceric sulfate stain; dialkylated material was observed at R$_f$0.21; $^1$H-NMR (300 MHz), CDCl$_3$): δ 8.19 (4 line m, 1H), 7.57 (11 line m, 2H), 7.40 (4 line m, 1H), 7.19 (m, 4H) , 4.17 (4 line m, 2H), 3.79 (3 line m, 1H), 3.19 (d, J=8.3 Hz, 2H), 2.66–2.32 (m, 2H), 1.54 (m, 2H), 1.28 (m, 2H), 1.24 (3 line m, 3H), 0.88 (3 line m, 3H ). Spectrum recorded after detritylation in MeOH/HCl.

2-[(2'-(N-TRIPHENYLMETHYL-TETRAZOL-5-YL)BIPHEN-4-YL)METHYL]-3-OXOHEPTANENITRILE

To a solution of 225 mg 3-oxoheptanenitrile in 10 mL DMSO was added 144 mg 60% NaH in oil. After two minutes 500 mg N-triphenylmethyl-5-[2-(4'-bromomethylbiphenyl)]tetrazole was added all at once to the solution. After 20 minutes the solution was poured into brine and extracted 3 times with ether. The organic material was dried over MgSO$_4$, stripped of solvent in vacuo, and MPLC'd in 15% EtOAc/hexane. The title compound was isolated as a white foam, 125 mg, 23% yield. R$_f$0.23 in 20% EtOAc/hexane, visualized by UV and ammonium molybdate/ceric sulfate stain; $^1$H-NMR (300 MHz, CDCl$_3$): δ 7.93 (m, 1H), 7.47 (10 line m, 2H), 7.40–7.20 (m, 10H), 7.04 (m, 4H), 6.90 (m, 6H), 3.44 (X of ABX, lit), 3.03 (AB of ABX, J$_{AB}$=13.8 Hz, JAX=8.6 HZ, JBX=5.3 Hz, ΔV=43.5 Hz, 2H), 2.59 (sym. 12 line m, 2H) , 1.55 (m, 2H), 1.28 (m, 2H) , 0.88 (t, J=7.3 Hz, 3H) .

EXAMPLE 1

Ethyl 2-[(2'-(N-triphenylmethyl-tetrazol-5-yl)biphen-4-yl)methyl]-3-(trifluoromethanesulfonato)-2(Z)-heptenoate The title compound is prepared by dissolving 1.0 equivalent of ethyl 2-[2'-(N-triphenyl-methyl-tetrazol-5-yl)biphen-4-yl)methyl]-3-oxoheptanoate in THF so that the solution is ~0.1–0.3M. To this is added 1.3 equivalents of sodium hydride. After 10 minutes a room temperature, 1.2 equivalents of trifluoromethanesulfonic anhydride is added. When the reaction is complete the mixture is neutralized with saturated NaHCO$_3$ solution and extracted with ether. The combined organic material is dried over MgSO$_4$, stripped of solvent in vacuo, and MPLC'd to give the title compound.

EXAMPLE 2

6-Butyl-2-methyl-5-[(2'-(N-triphenylmethyl-tetrazol-5-yl)biphen-4-yl)methyl]pyrimidin-4(3H)-one The title compound may be prepared by dissolving 1-5 equivalents of acetamidine hydrochloride and an equal mole-equivalent of sodium methoxide or sodium acetate in DMF. To this mixture is added 1.0 equivalent of ethyl 2-[(2'-(N-triphenyl-methyl-tetrazol-5-yl)biphen-4-yl)methyl]-3-(trifluoromethanesulfonato)-2(Z)-heptenoate. Enough DMF is used so the solution is ~0.1-1.0M in the heptenoate compound. The mixture is either stirred at RT or is heated to reflux, until complete. The mixture is poured into brine and extracted with ether. The combined organic material is dried over $MgSO_4$, stripped of solvent in vacuo, and MPLC'd to give the title compound.

EXAMPLE 3

6-Butyl-2-methyl-5-[(2'-(tetrazol-5-yl)biphen-4-yl)-methyl]pyrimidin-4-(3H)-one The title compound may be prepared by dissolving 6-butyl-2-methyl-5-[(2'-(N-triphenylmethyl-tetrazol-5-yl)biphen-4-yl)methyl]pyrimidin-4(3H)-one in methanol and adding excess concentrated HCl and stirring for 10-30 minutes. An indicator quantity of phenolphthalein is added followed by 10% NaOH solution until pink. Excess acetic acid is added and the mixture is extracted three times with ether. The combined organic material is dried over $MgSO_4$, stripped of solvent in vacuo, and MPLC'd to give the title compound.

EXAMPLE 4

6-Butyl-2-methyl-5-[(2'-(tetrazol-5-yl)biphen-4-yl)methyl]-4-trifluoromethanesulfonatopyrimidine To a solution of 1.0 equivalents of 6-butyl-2-methyl-5-[(2'-(tetrazol-5-yl)biphen-4-yl) methyl]pyrimidine-4(3H)-one and 5.0 equivalents of 2,4,6-collidine in methylene chloride at 0° C. is added 2.4 equivalents of trifluoromethanesulfonic anhydride. When the reaction is complete, the mixture is washed twice with saturated $CuSO_4$ solution, dried over $MgSO_4$, and stripped of solvent in vacuo.

EXAMPLE 5

6-Butyl-4-cyano-2-methyl-5-[(2'-(tetrazol-5-yl)biphen-4-yl)methyl]pyrimidine A solution of CuCN and 6-Butyl-2-methyl-5-[(2'-(tetrazol-5-yl)biphen-4-yl)methyl]-4-trifluoromethanesulfonatopyrimidine in pyridine is heated to give the title compound with standard brine workup.

EXAMPLE 6

6-Butyl-4-Carboxy-2-methyl-5-[(2'-(tetrazol-5-yl)biphen-4-yl)methyl]pyrimidine Heating 6-Butyl-4-cyano-2-methyl-5-[(2'-(tetrazol-5-yl)biphen-4-yl)methyl]pyrimidine with several equivalents of sodium hydroxide and excess hydrogen peroxide in methanol provides the corresponding primary amide after workup. Treatment of this material with concentrated HCl with warming following by an neutralization and extractive workup gives the title compound.

EXAMPLE 7

6-Butyl-4-methoxycarbonyl-2-methyl-5-[(2'(tetrazol-5-yl)biphen-4-yl)methyl]pyrimidin

Step A: Ethyl 2-[(4-iodophenyl)methyl]-3-oxoheptanoate

To a solution of 3.77 g (43.8 mmol) ethyl 3-oxoheptanoate in 200 mL DMSO was added 1.75 g (43.8 mmol) 65% NaH in oil. After 10 minutes, 6.5 g (21.9 mmol) α-bromo-4-iodotoluene was added. The mixture was allowed to stir for 2 hours. It was then poured into an ice/brine mixture and extracted 3 times with ether. The combined organic material was washed with brine, dried over $MgSO_4$, stripped of solvent in vacuo, then Still flash chromatographed in 40% $CH_2Cl_2$/hexane to give 2.46 g of the title compound, 29% yield. $R_f$ 0.23 in 40% $CH_2Cl_2$/hexane, visualized by UV and ninhydrin stain; $^1$H-NMR (300 MHz, $CDCl_3$): δ 7.58 (m,2H), 6.93 (m, 2H), 4.14 (m,2H), 3.72 (3 line m, 1H), 3.09 (m, 2H), 2.44 (12 line m, 2H), 1.50 (m, 2H), 1.22 (m, 2H), 1.21 (3 line m, 3H), 0.86 (3 line m, 3H).

Step B: 6-Butyl-2-methyl-5-[(4-iodophenyl)methyl]pyrimidine-4(3H)-one

A solution of 2.46 g (6.33 mmol) ethyl 2-[(4-iodophenyl)methyl]-3-oxoheptanoate, 6.0 g (63.3 mmol) acetamidine hydrochloride, 5.2 g (63.3 mmol) sodium acetate, and 84 mg (0.381 mmol) 2,6-di-tert-butyl-4-methylphenol in 30 mL DMF was heated to 153° C. for 12 hours. The cooled reaction mixture was poured into brine and extracted 3 times with ether. The combined organic material was washed with brine, dried over $MgSO_4$, stripped of solvent in vacuo, then was medium pressure chromatographed on silica gel using 1/65/34 AcOH/EtOAc/hexane to give 485 mg of the title compound, 20% yield. Unreacted ethyl 2-[(4-iodophenyl)-methyl]-3-oxoheptanoate was recycled. $R_f$ 0.25 in 1/65/34 AcOH/EtOAc/hexane, visualized by UV and ninhydrin stain; $^1$H-NMR (300 MHz, $CDCl_3$): δ 7.56 (m, 2H), 6.98 (m, 2H), 3.83 (s, 2H), 2.54 (3 line m, 2H), 2.38 (s, 3H), 1.52 (m, 2H), 1.43 (m, 2H), 0.89 (3 line m, 3H).

Step C: 6-Butyl-4-cyano-2-methyl-5-[(4-iodophenyl)methyl]pyrimidine

A solution of 485 mg (1.27 mmol) 6-butyl-2-methyl-5-[(4-iodophenyl)methyl]pyrimidine-4(3H)-one in 7 mL $POCl_3$ was refluxed for 60 minutes. After cooling to room temperature, excess $POCl_3$ was stripped off in vacuo. The crude product was partitioned between $CH_2Cl_2$ and a mixture of brine and $NaHCO_3$. The organic layer was removed and the aqueous layer was extracted three more times with $CH_2Cl_2$. The combined organic material was dried over $MgSO_4$, stripped of solvent in vacuo, then was medium pressure chromatographed on silica gel using 10% EtOAc/hexane to give 380 mg of 6-butyl-4-chloro-2-methyl-5-[(4-iodophenyl)methyl]pyrimidine, 75% yield.

To a solution of 380 mg (0.947 mmol) 6-butyl-4-chloro-2-methyl-5-[(4-iodophenyl)methyl]-pyrimidine in 10 mL acetone were added 0.119 mL 57% HI (0.900 mmol) and 851 mg (5.68 mmol) NaI. The mixture was warmed to 40° C. for 2.5 hours. As the reaction proceeds, NaCl can be seen precipitating out of solution. The mixture was diluted with brine and saturated $NaHCO_3$ solution. The mixture was extracted 3 times with ether. The combined organic material was dried over $MgSO_4$ and decolorized with activated charcoal, was stripped of solvent in vacuo, then was medium pressure chromatographed on silica gel using 10% EtOAc/hexane to give 440 mg of 6-butyl-4-iodo-2-methyl-5-[(4-iodophenyl)methyl]pyrimidine, 947% yield.

A mixture of 800 mg (8.94 mmol) CuCN and 10 mL pyridine was heated to 110° C. until all of the CuCN went into solution ( 7 minutes). To this mixture was added a solution of 440 mg (0.894 mmol) 6-butyl-4-iodo-2-methyl-5-[(4-iodophenyl)methyl]pyrimidine in 3 mL pyridine. After 5 minutes, the reaction mixture was cooled to room temperature, diluted with CH$_2$Cl$_2$, filtered through powdered cellulose flock, stripped of solvent in vacuo, and was medium pressure chromatographed on silica gel using 13% EtOAc/hexane to give 306 mg of the title compound, 87% yield. R$_f$ 0.29 in 15% EtOAc/hexane, visualized by UV and ammonium molybdate/ceric sulfate stain; $^1$H-NMR (300 MHz, CDCl$_3$): δ 7.63 (m, 2H), 6.84 (m, 2H), 4.16 (s, 2H), 2.73 (s, 3H), 2.68 (3 line m, 2H), 1.53 (m, 2H), 1.31 (m, 2H), 0.87 (3 line m, 3H).

Step D: 6-Butyl-4-methoxycarbonyl-2-methyl-5-[(4-iodophenyl)methyl]pyrimidine

To a solution of 306 mg 6-butyl-4-cyano-2-methyl-5-[(4-iodophenyl)methyl]pyrimidine in 6 mL methanol was added 0.885 mL (~7.81 mmol) 30% H$_2$O$_2$ and 0.937 mL (2.34 mmol) 2.5 N NaOH. The mixture was allowed to stir for 1 hour at room temperature. To the mixture was added ~1 mL HOAc. Solvent was removed in vacuo. The crude material (409 mg) was dissolved in ~20 mL methanol. To this was added 4.0 g Amberlyst-15 ®. The mixture was heated to 60° for 18 hours. After cooling to room temperature, ~5 mL pyridine was added. After stirring for 1 hour, the mixture was filtered through powdered cellulose flock, stripped of solvent in vacuo, stripped from toluene to remove remaining pyridine, then was medium pressure chromatographed on silica gel using 25% EtOAc/hexane to give 152 mg of the title compound, 46% yield. R$_f$ 0.21 in 30% EtOAc/hexane, visualized by UV and ammonium molybdate/ceric gulfate stain; $^1$H-NMR (300 MHz, CDCl$_3$); δ 7.58 (m, 2H0, 6.81 (m, 2H), 4.12 (s, 2H), 3.87 (s, 3H), 2.75 (s, 3H), 2.67 (3 line m, 2H), 1.53 (m, 2H), 1.31 (m, 2H), 0.86 (3 line m, 3H).

Step E: 6-Butyl-4-methoxycarbonyl-2-methyl-5-[(2'-tetrazol-5-yl)biphen-4-yl)methyl]-pyrimidine To −25° C. solution of 278 mg (0.717 mmol) 5-phenyl-2-triphenylmethyltetrazole in 4 mL THF was added dropwise a solution of 1.7M tert-butyllithium in pentane until a faint red color persisted (drying process). Then 0.420 mL (0.717 mmol) of the 1.7 M tert-butyllithium in pentane was added. After 2 minutes the solution was blood red. After 25 minutes, the organolithium salt was precipitating from the THF. At this time, 0.358 mL (0.358 mmol) 1.0M ZnCl$_2$ in ether was added. The color changed from blood red to medium yellow and the precipitate went back into solution. The mixture was warmed to room temperature. To the solution was added 13 mg (0.018 mmol) (Ph$_3$P)$_2$PdCl$_2$ followed by 152 mg (0.358 mmol) 6-butyl-4-methoxycarbonyl-2-methyl-5-[(4-iodophenyl)methyl]pyrimidine. The mixture was refluxed for 3.25 hours then cooled to room temperature, diluted with water and brine, and was extracted 3 times with ether. The combined organic material was dried over MgSO$_4$, stripped of solvent in vacuo, then was medium pressure chromatographed on silican gel using 30% EtOAc/hexane to give 146 mg of the trityl protected title compound, 60% yield. R$_f$ 0.18 in 30% EtOAc/hexane, visualized by UV and ammonium molybdate/ceric sulfate stain.

A solution of 146 mg of the trityl protected title compound in 4/1/1 AcOH/H$_2$O/CH$_2$Cl$_2$ was stirred for 6 hours at room temperature. The mixture was diluted with brine and extracted 3 times with CH$_2$Cl$_2$. The combined organic material was dried over MgSO$_4$, stripped of solvent in vacuo, stripped from toluene, then was Still flash chromatographed in 1/13/86 NH$_4$OH/MeOH/CH$_2$Cl$_2$ to give 92 mg of the title compound, 97% yield. R$_f$ 0.18 in 1/50/49 AcOH/EtOAc/hexane; R$_f$ 0.22 in 1/13/86 NH$_4$OH/MeOH/CH$_2$Cl$_2$, visualized by UV; $^1$H-NMR (300 MHz, CDCl$_3$): δ 8.10 (m, 1H), 7.57 (m, 2H), 7.37 (m, 1H), 7.04 (m, 4H), 4.24 (s, 2H), 3.79 (s, 3H), 2.67 (3 line m, 2H), 2.53 (s, 3H), 1.58 (m, 2H), 1.34 (m, 2H), 0.88 (3 line m, 3H); MS (FAB) m/e 443 (M+1).

EXAMPLE 8

6-Butyl-4-carboxy-2-methyl-5-[(2'-(tetrazol-5-yl)-biphen-4-yl)methyl]pyrimidine

To a solution of 68 4 mg (0.155 manol) 6-butyl-4-methoxycarbonyl-2-methyl-5-[(2'-(tetrazol-5-yl)biphen-4-yl)methyl]pyrimidine in 5 mL methanol was added ~0.300 mL 10% NaOH. After stirring at room temperature for 2.5 hours, the mixture was acidified with ~0.500 mL HOAc. Volatiles were removed in vacuo. The crude material was redissolved in methanol along with a couple of drops of TFA, then was HPLC'd using the following conditions: Rainin Dynamax ® C-18 column, 25×2.14 cm w/Guard Column; gradient of acetonitrile in water 5 to 100% over 40 minutes at 5 mL/minute; gradient held at 82% for 7 minutes. A yield of 66.1 mg (100%) of the title compound was obtained. R$_f$ 0.14 in 1/30/69 NH$_4$OH/MeOH/CH$_2$Cl$_2$, visualized by UV; $^1$H-NMR (300 MHZ, CDCl$_3$): δ~9.7–8.8 (v br s 2H) 7.97 (m, 1H), 7.52 (m, 2H), 7.37 (m, 1H), 7.00 (br s, 4H), 4.51 (br s, 2H), 2.86 (3 line m, 2H), 2.75 (br s, 3H), 1.62 (m, 2H), 1.36 (m, 2H), 0.88 (3 line m, 3H); MS(FAB) m/e 429 (M+1).

EXAMPLE 9

6-Butyl-6-methyl-3-[(2'-(tetrazol-5-yl)biphen-4-yl)-methyl]-4H-pyrido[1,2-a]pyrimidine-4-one Step A: 2-Butyl-3-[(4-iodophenyl)methyl]-6-methyl-4H-pyrido[1,2-a]pyrimidin-4-one A mixture of 1.59 g (4.09 mmol) ethyl 2-[(4-iodophenyl)methyl]-3-oxoheptanoate, 487 mg (4.50 mmol) 2-amino-5-methylpyridine, and 3 g PPA was heated to 160° C. for 1 hour. The mixture was cooled to room temperature then NH$_4$OH was added with cooling. When all of the PPA had reacted, the mixture was extracted e times with ether. The cominbed organic material was dried over MgSO$_4$, stripped of solvent in vacuo, then Still flash chromatographed in 10/50/40 EtOAc/CH$_2$Cl$_2$/hexane to give 177 mg of the title compound, 10% yield. R$_f$ 0.21 in 10/50/40 EtOAc/CH$_2$Cl$_2$/hexane, visualized by UV; $^1$H-NMR (300 MHz, CDCl$_3$): δ 8.80 (s, 1H), 7.55 (m, 2H), 7.51 (s, 2H), 7.02 (m, 2H), 4.05 (s, 2H), 2.72 (3 line m, 2H), 2.40 (s, 3H), 1.61 (m, 2H), 1.39 (m, 2H), 0.91 (3 line m, 3H).

Step B: 2-Butyl-6-methyl-3-[(2'--(tetrazol-5---yl)-biphen-4-yl)methyl]-4H-pyrido[1,2-a3-pyrimidin-4-One To −25° C. solution of 318 mg (0.819 mmol) 5-phenyl-2-triphenylmethyltetrazole in 5 mL THF was added dropwise a solution of 1.7 M tert-butyllithium in pentane until a faint red color persisted (drying process). Then 0.482 mL (0.819 mmol) of the 1.7M tert-butyllithium in pentane was added. After 2 minutes the solution was blood red. After 30 minutes, the organolithium salt was precipitating from the THF. At this time, 0.410 mL (0.410 mmol) 1.0M ZnCl₂ in ether was added. The color changed from blood red to medium yellow and the precipitate went back into solution. The mixture was warmed to room temperature. To the solution was added 14 mg (0.020 mmol) (Ph₃P)₂PhCl₂ followed by 177 mg (0.410 mmol) 2-butyl-3-[(4-iodophenyl)methyl]-6-methyl-4H-pyrimidin-4-one. The mixture was refluxed for 4 hours then was cooled to room temperature, diluted with water and brine, and was extracted 3 times with ether. The combined organic material was dried over MgSO₄, stripped of solvent in vacuo, then was medium pressure chromatographed on silica gel using 40% EtOAc/hexane to give 159.4 mg of the trityl protected title compound, 56% yield. $R_f$ 0.18 in 40% EtOAc/hexane, visualized by UV and ammonium molybdate/ceric sulfate stain.

To a solution of 159.4 mg of the trityl protected title compound in 5 mL methanol was added 10 drops concentrated HCl. After 30 minutes, an indicator quantity of phenolphthalein was added and the mixture was basified with 10% NaOH then reacidified with HOAc. Ether was added and the mixture was dried over MgSO₄, stripped of solven in vacuo, then was Still flash chromatographed in 1/12/87 NH₄OH/MeOH/CH₂Cl₂ to give 95.7 mg of the title compound as its ammonium salt, 89% yield. $R_f$ 0.22 in 1/13/86 NH₄OH/MeOH/CH₂Cl₂, visualized by UV; ¹H-NMR (300 MHz, CDCl₃): δ 8.78 (s, 1H), 8.13 (m, 1H), 7.53 (m, 4H), 7.37 (m, 1H), 7.17 (m, 2H), 7.06 (m, 2H), ~6.1-5.0 (v br s, 4H), 4.06 (s, 2H), 2.75 (3 line m, 2H), 2.39 (s, 3H), 1.67 (m, 2H), 1.41 (m, 2H), 0.92 (3 line m, 3H); MS (FAB) m/3 451 (M+1).

EXAMPLE 10

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 6-butyl-4-carboxy-2-methyl-5-[(2'-(tetrazol-5-yl)biphen-4-yl)methyl]-pyrimidine | 50 |
| Lactose | 149 |
| Magnesium stearate Capsule (size No. 1) | 1 |
| | 200 |

The 6-butyl-4-carboxy-2-methyl-5-[(2'-(tetrazol-5-yl)biphen-4-yl)methyl]pyrimidine can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 6-butyl-4-carboxy-2-methyl-5-[(2'-(tetrazol-5-yl)biphen-4-yl)-methyl]pyrimidine (25 mg), pregelatinized starch USP (82 mg), microcrystaline cellulose (82 mg) and magnesium stearate (1 mg).

Combination Tablet

A typical combination tablet would contain, for example, 6-butyl-4-carboxy-2-methyl-5-[(2'-(tetrazol-5-yl)biphen-4-yl)methyl]pyrimidine a diuretic such as hydrochlorothiazide and consist of hydrochlorothiazide (50 mg) pregelatinized starch USP (82 mg), microcrystalline cellulose (82 mg) and magnesium stearate (1 mg).

D: Suppository

Typical suppository formulations for rectal administration can contain 6-butyl-4-carboxy-2-methyl-5-[(2'-(tetrazol-5-yl)biphen-4-yl)methyl]pyrimidine (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation would contain 6-butyl-4-carboxy-2-methyl-5-[(2'-(tetrazol-5-yl)biphen-4-yl)methyl]pyrimidine, sodium phosphate dibasic anhydrous (11.4 mg) benzylalcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula:

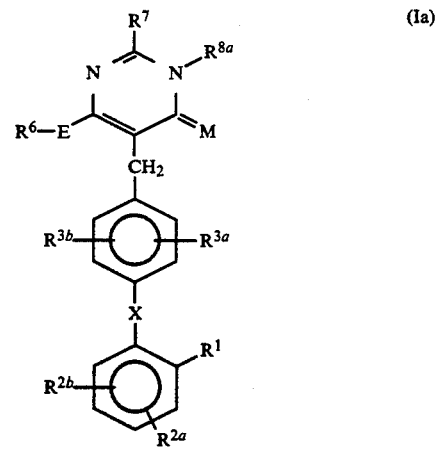

(Ia)

or a pharmaceutically acceptable salt thereof,
wherein:
M is O or NR²²;
R¹ is
(a) —CO₂R⁴,
(b) —SO₃R⁵,
(c) —NHSO₂CF₃,
(d) —PO(OR⁵)₂,
(e) —SO—NH—R⁹,
(f) —CONHOR⁵, (g) 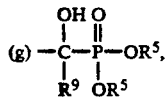

(h) —CN,
(i) —SO$_2$NH-heteroaryl, wherein heteroaryl is defined below,
(j) —CH$_2$SO$_2$NH-heteroaryl, wherein heteroaryl is defined below,
(k) —SO$_2$NH—CO—R$^{23}$,
(l) —CH$_2$SO$_2$NH—CO—R$^{23}$,
(m) —CONH—SO$_2$R$^{23}$,
(n) —CH$_2$CONH—SO$_2$R$^{23}$,
(o) —NHSO$_2$NHCO—R$^{23}$,
(p) —NHCONHSO$_2$—R$^{23}$, (q) 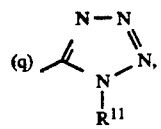

(r) —CH$_2$ 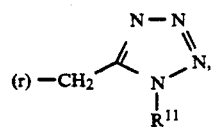

(s) —CON 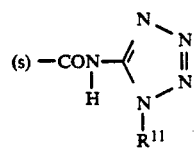
    H

(t) —CONHNHSO$_2$CF$_3$, (u) 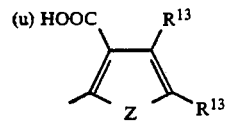

(v) 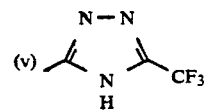

(w) 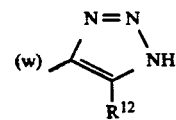

wherein heteroaryl is an unsubstituted, monosubstituted or disubstituted tetrazolyl or pyridyl aromatic ring, wherein the substituents are members selected from the group consisting of —OH, —SH, —C$_1$-C$_4$-alkyl, —C$_1$-C$_4$-alkoxy, —CF$_3$, Cl, R, F, I, —NO$_2$, —CO$_2$—C$_1$-C$_4$-alkyl, —NH$_2$, NH(C$_1$-C$_4$-alkyl) and —N(C$_1$-C$_4$-alkyl)$_2$;

R$^{2a}$ and R$^{2b}$ are each independently
(a) H,
(b) halogen,
(c) NO$_2$,
(d) NH$_2$,
(e) C$_1$-C$_4$-alkylamino,
(f) di-(C$_1$-C$_4$-alkyl)amino,
(g) SO$_2$NHR$^9$,
(h) CF$_3$,
(i) C$_1$-C$_4$-alkyl, or
(j) C$_1$-C$_4$-alkoxy;

R$^{3a}$ is
(a) H,
(b) Cl, Br, I, F,
(c) C$_1$-C$_6$-alkyl
(d) C$_1$-C$_6$-alkoxy,
(e) C$_1$-C$_6$-alkoxy-C$_1$-C$_4$-alkyl;

R$^{3b}$ is
(a) H,
(b) Cl, Br, I, F,
(c) NO$_2$,
(d) C$_1$-C$_6$-alkyl,
(e) C$_2$-C$_6$-alkanoyloxy,
(f) C$_3$-C$_6$-cycloalkyl,
(g) C$_1$-C$_6$-alkoxy,
(h) —NHSO$_2$R$^4$,
(i) hydroxy-C$_1$-C$_4$-alkyl,
(j) aryl-C$_1$-C$_4$-alkyl,
(k) C$_1$-C$_4$-alkylthio,
(l) C$_1$-C$_4$-alkylsulfinyl,
(m) C$_1$-C$_4$-alkylsulfonyl,
(n) NH$_2$,
(o) C$_1$-C$_4$-alkylamino,
(p) C$_1$-C$_4$-dialkylamino,
(q) CF$_3$,
(r) —SO$_2$—NHR$^9$,
(s) aryl, wherein aryl is defined below, or
(t) furyl;

wherein aryl is phenyl or naphthyl unsubstituted or substituted with one or two substituents selected from the group consisting of Cl, Br, I, F, C$_1$-C$_4$-alkyl, C$_1$-C$_4$-alkoxy, NO$_2$, CF$_3$, C$_1$-C$_4$-alkylthio, OH, NH, —NH(C$_1$-C$_4$-alkyl), —N(C$_1$-C$_4$-alkyl)$_2$, —CO$_2$H, C$_1$-C$_4$-polyfluoroalkyl, C$_3$-C$_6$-polyfluorocycloalkyl, —CO$_2$—C$_1$-C$_4$-alkyl or

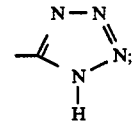

R$^4$ is H, C$_1$-C$_6$-alkyl, benzyl or phenyl;

R$^5$ 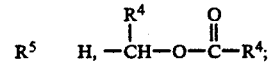

E is single bond, —NR$^{13}$(CH$_2$)$_s$—, —S(O)$_x$(CH$_2$)$_s$— where x is 0 to 2 and s is 0 to 5, —CH(OH)—, —O—, CO—;

R$^6$ is
(a) C$_1$-C$_6$-alkyl, C$_2$-C$_5$-alkenyl or C$_2$-C$_5$-alkynyl each of which can be optionally substituted with a substituent selected from the group consisting of aryl as defined above, C$_3$-C$_7$-cycloalkyl, Cl, Br, I, F, —OH, CF$_3$CCl$_3$, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$, C$_1$-C$_4$-alkoxy, C$_1$-C$_4$-alkyl-S, and —CF$_2$CF$_3$;
(b) C$_3$-C$_5$-cycloalkyl;
(c) polyfluoro-C$_1$-C$_4$-alkyl;

R$^7$ and R$^{8a}$ are joined together with the atoms to which they are bound to form a pyridine ring which may be substituted with $R^{26}$ and/or $R^{27}$ wherein
$R^{26}$ is
(b) —NHCO($C_1$-$C_4$-alkyl),
(c) —NHCO($C_3$-$C_6$-cycloalkyl),
(d) —NHCO(aryl), wherein aryl is defined above,
(e) —NHCO(heteroaryl), wherein heteroaryl is defined above,
(f) —N($C_1$-$C_5$-alkyl)CO($C_1$-$C_5$-alkyl),
(g) —N($C_1$-$C_5$-alkyl)CO($C_3$-$C_6$-cycloalkyl),
(h) —N($C_1$-$C_5$-alkyl)CO(aryl), wherein aryl is defined above,
(i) —N($C_1$-$C_5$-alkyl)CO(heteroaryl), wherein heteroaryl is defined above;
$R^{27}$ is $C_1$-$C_4$-alkyl, Cl, Br, F, I, —$CF_3$, aryl or heteroaryl, wherein aryl and heteroaryl are both defined above;
$R^9$ is H, $C_1$-$C_5$-alkyl, phenyl or benzyl;
$R^{10}$ is H, $C_1$-$C_4$-alkyl;
$R^{11}$ is H, $C_1$-$C_6$-alkyl, $C_2$-$C_4$-alkenyl, $C_1$-$C_4$-alkoxyalkyl, or —$CH_2$—$C_6H_4R^{20}$;
$R^{12}$ is —CN, —$NO_2$, —$CO_2R^4$, or —$CF_3$;
$R^{13}$ is H, $C_2$-$C_4$-alkanoyl, $C_1$-$C_6$-alkyl, allyl, $C_3$-$C_6$-cycloalkyl, phenyl or benzyl,
$R^{14}$ is H, $C_1$-$C_8$-alkyl, $C_1$-$C_8$-perfluoroalkyl, $C_3$-$C_6$-cycloalkyl, phenyl or benzyl;
$R^{15}$ is H, $C_1$-$C_6$-alkyl;
$R^{16}$ is H, $C_1$-$C_6$-alkyl, $C_3$-$C_6$-cycloalkyl, phenyl or benzyl;
$R^{17}$ is —$NR^9R^{10}$, —$OR^{10}$, —$NHCONH_2$, —$NHCSNH_2$,

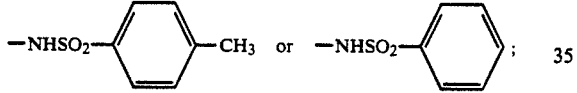

$R^{18}$ and $R^{19}$ are independently $C_1$-$C_4$-alkyl or taken together are —$(CH_2)_q$— where q is 2 or 3;
$R^{20}$ is H, —$NO_2$, —$NH_2$, —OH or —$OCH_3$;
$R^{21}$ is
(a) —CO-aryl, wherein aryl is defined above,
(b) —CO—$C_1$-$C_4$-alkyl,
(c) —$COCF_3$,
(d) —CO-heteroaryl, wherein heteroaryl is defined above, or
(e) heteroaryl; wherein heteroaryl is defined above;
$R^{22}$ is —H; or
(a) aryl, wherein aryl is defined above,
(b) heteroaryl, wherein heteroaryl is defined above,
(c) $C_1$-$C_4$-alkyl either unsubstituted or substituted with aryl, wherein aryl is defined above, wherein heteroaryl is defined above, —OH, —$NH_2$, —NH($C_1$-$C_4$-alkyl), N($C_1$-$C_4$-alkyl)$_2$, —$CO_2H$, —$CO_2R^4$, Cl, Br, I, or F, or
(d) $C_1$-$C_4$-alkylaryl either unsubstituted or substituted with $CO_2R^4$;
$R^{23}$ is
(a) aryl, wherein aryl is defined above,
(b) heteroaryl, wherein heteroaryl is defined above,
(c) $C_3$-$C_7$-cycloalkyl,
(d) $C_1$-$C_6$-alkyl unsubstituted or substituted with a substituent selected from the group consisting of aryl, wherein aryl is defined above, heteroaryl, wherein aryl is defined above, —OH, —SH, —$C_1$-$C_4$-alkyl, —O($C_1$-$C_4$-alkyl), —S($C_1$-$C_4$-alkyl), —$CF_3$, Cl, Br, F, I, —$NO_2$, —$CO_2H$, —$CO_2$—$C_1$-$C_4$-alkyl, —$NH_2$, —NH($C_1$-$C_4$-alkyl), —N($C_1$-$C_4$-alkyl)$_2$, —$PO_3H_2$, or —PO(OH) (O—$C_1$-$C_4$-alkyl);

$R^{25}$ is
(a) H,
(b) $C_1$-$C_4$-alkyl;
X is
(a) a carbon-carbon single bond,
(b) —CO—,
(c) —O—,
(d) —S—,
(e) —N—, (f) 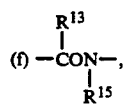

(g) 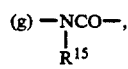

(h) —$OCH_2$—,
(i) —$CH_2O$—,
(j) —$SCH_2$—,
(k) —$CH_2S$—,
(l) —NHC($R^9$)($R^{10}$)—,
(m) —$NR^9SO_2$—,
(n) —$SO_2NR^9$—,
(o) —C($R^9$)($R^{10}$)NH—,
(p) —CH=CH—,
(q) —CF=CF—,
(r) —CH=CF—,
(s) —CF=CH—,
(t) —$CH_2CH_2$—,
(u) —$CF_2CF_2$—, (v) 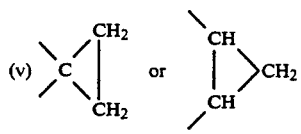

(w) 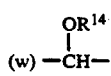

(x) 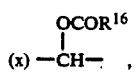

(y) 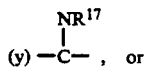, or (z) 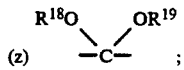;

Z is O, $NR^{13}$ or S.

2. The compound of claim 1 wherein K is —N(-$R^{8a}$)—CO— of structure

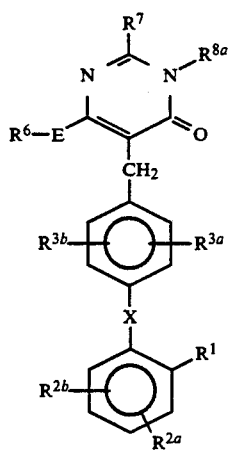

3. The compound of claim 1 wherein R¹ is —COOH;

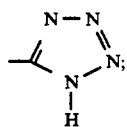

—NH—SO₂CF₃; CO₂R⁴; —SO₂NH—heteroaryl or CH₂SO₂NH—heteroaryl wherein the heteroaryl is an unsubstituted, monosubstituted or disubstituted 5- or 6-membered aromatic ring comprising 1 to 3 heteroatoms selected from O, N and S and wherein the substituents are members selected from the group consisting of OH, SH, $C_1$-$C_4$-alkyl, $C_1$-$C_4$-alkoxy, $CF_3$, Cl, Br, F, I, $NO_2$, $CO_2H$, $CO_2$—$C_1$-$C_4$-alkyl, $NH_2$, $NH(C_1$-$C_4$-alkyl) and $N(C_1$-$C_4$-alkyl)$_2$; —SO₂NHCOR²³; —CH₂SO₂NHCOR²³; —CONHSO₂R²³; —CH₂CONHSO₂R²³; —NHSO₂NHCOR²³; and —NHCONHSO₂R²³;

R²ᵃ and R²ᵇ are H, F, Cl, CF₃, $C_1$-$C_4$-alkyl or $C_1$-$C_4$-alkoxy;

R³ᵃ is H, F, or Cl;

R³ᵇ is H, F, Cl, CF₃, $C_1$-$C_4$-alkyl, $C_1$-$C_4$-alkoxy, —COOCH₃, —COOC₂H₅, —SO₂—CH₃, NH₂, —N($C_1$-$C_4$-alkyl)₂ or —NH—SO₂CH₃;

E is a single bond, —O— or —S—;

R⁶ is (a) $C_1$-$C_5$-alkyl, $C_2$-$C_5$-alkenyl or $C_2$-$C_5$-alkynyl each of which can be substituted with a substituent selected from the group consisting of Cl, CF₃, CF₂CF₃, CCl₃, —O—CH₃, —OC₂H₅, —S—CH₃, —S—C₂H₅, phenyl and $C_3$-$C_5$-cycloalkyl;

(b) $C_3$-$C_5$-cycloalkyl;

(c) polyfluoro-$C_1$-$C_4$-alkyl;

X is a C—C single bond wherein heteroaryl is defined as in claim 1.

4. The compound of claim 1 wherein:

E is a single bond;

R²ᵃ, R²ᵇ, R³ᵃ and R³ᵇ are each H; and

X is a single bond.

5. The compound of claim 1 which is a member of the group of compound of Formula IV and described in table 3:

TABLE 3

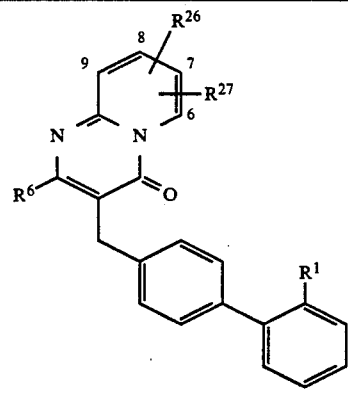

IV

| Compd. No. | R¹ | R⁶ | R²⁶ | R²⁷ |
|---|---|---|---|---|
| IV-1 | tetrazol-5-yl | Bu | H | 7-Me |
| IV-2 | tetrazol-5-yl | Bu | H | 7-ⁱPr |
| IV-3 | tetrazol-5-yl | Pr | H | 7-N(Pen)COPh |
| IV-4 | tetrazol-5-yl | Pr | H | 7-N(Pen)CO(4-Cl—Ph) |
| IV-5 | tetrazol-5-yl | Pr | H | 7-N(Pr)CO₂—ⁱBu |
| IV-6 | tetrazol-5-yl | Pr | H | 7-N(Bn)COBu |
| IV-7 | tetrazol-5-yl | Bu | 8-Cl | 7-SO₂Me |
| IV-8 | tetrazol-5-yl | Bu | H | 8-Cl |
| IV-9 | —NHSO₂CF₃ | Bu | H | 7-Me |
| IV-10 | —NHSO₂CF₃ | Bu | H | 7-ⁱPr |
| IV-11 | —NHSO₂CF₃ | Pr | H | 7-N(Pen)COPh |
| IV-12 | —NHSO₂CF₃ | Pr | H | 7-N(Pen)CO(4-Cl—Ph) |
| IV-13 | —NHSO₂CF₃ | Pr | H | 7-N(Pr)CO₂—ⁱBu |
| IV-14 | —NHSO₂CF₃ | Pr | H | 7-N(Bn)COBu |
| IV-15 | —NHSO₂CF₃ | Bu | 8-Cl | 7-SO₂Me |
| IV-16 | —NHSO₂CF₃ | Bu | H | 8-Cl |
| IV-17 | —SO₂NHCOᶜʸPr | Bu | H | 7-Me |
| IV-18 | —SO₂NHCOᶜʸPr | Bu | H | 7-ⁱPr |
| IV-19 | —SO₂NHCOᶜʸPr | Pr | H | 7-N(Pen)COPh |

TABLE 3-continued

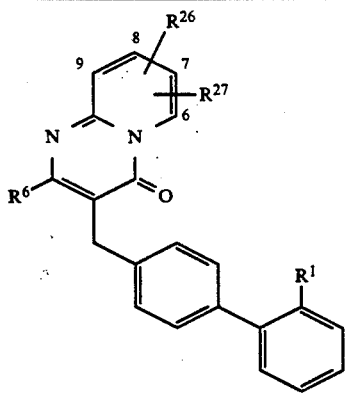

| Compd. No. | R¹ | R⁶ | R²⁶ | R²⁷ |
|---|---|---|---|---|
| IV-20 | —SO₂NHCO$^c$Pr | Pr | H | 7-N(Pen)CO(4-Cl—Ph) |
| IV-21 | —SO₂NHCO$^c$Pr | Pr | H | 7-N(Pr)CO₂—$^i$Bu |
| IV-22 | —SO₂NHCO$^c$Pr | Pr | H | 7-N(Bn)COBu |
| IV-23 | —SO₂NHCO$^c$Pr | Bu | 8-Cl | 7-SO₂Me |
| IV-24 | —SO₂NHCO$^c$Pr | Bu | H | 8-Cl |
| IV-25 | —SO₂NHCOPh | Bu | H | 7-Me |
| IV-26 | —SO₂NHCOPh | Bu | H | 7-$^i$Pr |
| IV-27 | —SO₂NHCOPh | Pr | H | 7-N(Pen)COPh |
| IV-28 | —SO₂NHCOPh | Pr | H | 7-N(Pen)CO(4-Cl—Ph) |
| IV-29 | —SO₂NHCOPh | Pr | H | 7-N(Pr)CO₂—$^i$Bu |
| IV-30 | —SO₂NHCOPh | Pr | H | 7-N(Bn)COBu |
| IV-31 | —SO₂NHCOPh | Bu | 8-Cl | 7-SO₂Me |
| IV-32 | —SO₂NHCOPh | Bu | H | 8-Cl |
| IV-33 | —SO₂NHCO—(CH₂)₅NH₂ | Bu | H | 7-$^i$Pr |
| IV-34 | —SO₂NHCO—(CH₂)₅NH₂ | Bu | 8-Cl | 7-SO₂Me |
| IV-35 | —SO₂NHCO—(CH₂)₅NH₂ | Bu | H | 8-Cl |
| IV-36 | —SO₂NHCO—(CH₂)₅NH₂ | Pr | H | 7-N(Pen)CO(4-Cl—Ph) |
| IV-37 | —SO₂NHCO—(CH₂)₅NH₂ | Pr | H | 7-N(Pr)CO₂—$^i$Bu |
| IV-38 | —SO₂NHCO—(CH₂)₅NH₂ | Pr | Me | 2-CF₃-phenyl |
| IV-39 | —SO₂NHCO—(CH₂)₅NH₂ | Pr | —CF₂CF₃ | 2-Cl-phenyl |

6. The compound of claim 1 wherein K is —N(-R$^{8a}$)—C(=NR$^{22}$)—of structure

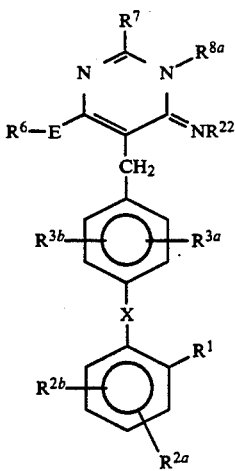

7. The compound of claim 1 wherein:
R¹ is —COOH;

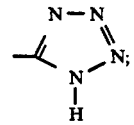

—NH—SO₂CF₃; CO₂R⁴; —SO₂NH-heteroaryl or —CH₂SO₂NH-heteroaryl wherein the heteroaryl is an unsubstituted, or monosubstituted or disubstituted 5- or 6-membered aromatic ring comprising 1 to 3 heteroatoms selected from O, N and S and wherein the substituents are members selected from the group consisting of OH, SH, C₁-C₄-alkyl, C₁-C₄-alkoxy, CF₃, Cl, Br, F, I, NO₂, CO₂H, CO₂—C₁-C₄-alkyl, NH₂, NH(C₁-C₄-alkyl) and N(C₁-C₄-alkyl)₂; —SO₂NHCOR²³; —CH₂SO₂NHCOR²³; —CONHSO₂R²³; —CH₂CONHSO₂R²³; —NHSO₂NHCOR²³; and —NHCONHSO₂R²³;

R²$^a$ and R²$^b$ are H, F, Cl, CF₃, C₁-C₄-alkyl or C₁-C₄-alkoxy;

R³$^a$ is H, F, or Cl;

R³$^b$ is H, F, Cl, CF₃, C₁-C₄-alkyl, C₅-C₆-cycloalkyl, —COOCH₃, —COOC₂H₅, —SO₂CH₃, NH₂, —N(C₁-C₄-alkyl)₂ or —NH—SO₂CH₃;

E is a single bond, —O— or —S—;

R⁶ is (a) C₁-C₅-alkyl, C₂-C₅-alkenyl or C₂-C₅-alkynyl each of which can be substituted with a substituent selected from the group consisting of Cl, CF₃, CCl₃, —O—CH₃, —OC₂H₅, —S—CH₃, —S—C₂H₅, phenyl, and C₃-C₅-cycloalkyl;

(b) C₃-C₅-cycloalkyl; or (c) polyfluoro-C₁-C₄-alkyl;

X is a C—C single bond wherein heteroaryl is defined as in claim 1.

8. The compound of claim 1 wherein:
E is a single bond;
R²ᵃ, R²ᵇ, R³ᵃ and R³ᵇ are each H; and
X is a single bond.

9. The compound of claim 1 which is a member selected from the group consisting of compounds of Formula VI and described in Table 5:

TABLE 5

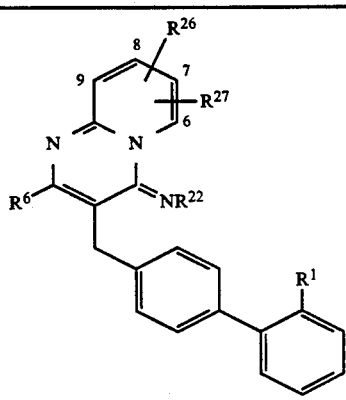

VI

| Compd. No. | R¹ | R⁶ | R²² | R²⁶ | R²⁷ |
|---|---|---|---|---|---|
| VI-1 | tetrazol-5-yl | Bu | cʸPr | H | 7-Me |
| VI-2 | tetrazol-5-yl | Bu | cʸPr | H | 7-ⁱPr |
| VI-3 | tetrazol-5-yl | Pr | Me | H | 7-N(Pen)COPh |
| VI-4 | tetrazol-5-yl | Pr | Me | H | 7-N(Pen)CO(4-Cl—Ph) |
| VI-5 | tetrazol-5-yl | Pr | Me | H | 7-N(Pr)CO₂—ⁱBu |
| VI-6 | tetrazol-5-yl | Pr | Me | H | 7-N(Bn)COBu |
| VI-7 | tetrazol-5-yl | Bu | cʸPr | 8-Cl | 7-SO₂Me |
| VI-8 | tetrazol-5-yl | Bu | cʸPr | H | 8-Cl |
| VI-9 | —NHSO₂CF₃ | Bu | cʸPr | H | 7-Me |
| VI-10 | —NHSO₂CF₃ | Bu | cʸPr | H | 7-ⁱPr |
| VI-11 | —NHSO₂CF₃ | Pr | Me | H | 7-N(Pen)COPh |
| VI-12 | —NHSO₂CF₃ | Pr | Me | H | 7-N(Pen)CO(4-Cl—Ph) |
| VI-13 | —NHSO₂CF₃ | Pr | Me | H | 7-N(Pr)CO₂—ⁱBu |
| VI-14 | —NHSO₂CF₃ | Pr | Me | H | 7-N(Bn)COBu |
| VI-15 | —NHSO₂CF₃ | Bu | cʸPr | 8-Cl | 7-SO₂Me |
| VI-16 | —NHSO₂CF₃ | Bu | cʸPr | H | 8-Cl |
| VI-17 | —SO₂NHCOcʸPr | Bu | cʸPr | H | 7-Me |
| VI-18 | —SO₂NHCOcʸPr | Bu | cʸPr | H | 7-ⁱPr |
| VI-19 | —SO₂NHCOcʸPr | Pr | Me | H | 7-N(Pen)COPh |
| VI-20 | —SO₂NHCOcʸPr | Pr | Me | H | 7-N(Pen)CO(4-Cl—Ph) |
| VI-21 | —SO₂NHCOcʸPr | Pr | Me | H | 7-N(Pr)CO₂—ⁱBu |
| VI-22 | —SO₂NHCOcʸPr | Pr | Me | H | 7-N(Bn)COBu |
| VI-23 | —SO₂NHCOcʸPr | Bu | cʸPr | 8-Cl | 7-SO₂Me |
| VI-24 | —SO₂NHCOcʸPr | Bu | cʸPr | H | 8-Cl |
| VI-25 | —SO₂NHCOPh | Bu | cʸPr | H | 7-Me |
| VI-26 | —SO₂NHCOPh | Bu | cʸPr | H | 7-ⁱPr |
| VI-27 | —SO₂NHCOPh | Pr | Me | H | 7-N(Pen)COPh |
| VI-28 | —SO₂NHCOPh | Pr | Me | H | 7-N(Pen)CO—(4-Cl—Ph) |
| VI-29 | —SO₂NHCOPh | Pr | Me | H | 7-N(Pr)CO₂—ⁱBu |
| VI-30 | —SO₂NHCOPh | Pr | Me | H | 7-N(Bn)COBu |
| VI-31 | —SO₂NHCOPh | Bu | cʸPr | 8-Cl | 7-SO₂Me |
| VI-32 | —SO₂NHCOPh | Bu | cʸPr | H | 8-Cl |
| VI-33 | —SO₂NHCO—(CH₂)₅NH₂ | Bu | cʸPr | H | 7-Pr |
| VI-34 | —SO₂NHCO—(CH₂)₅NH₂ | Bu | cʸPr | 8-Cl | 7-SO₂Me |
| VI-35 | —SO₂NHCO—(CH₂)₅NH₂ | Bu | cʸPr | H | 8-Cl |
| VI-36 | —SO₂NHCO—(CH₂)₅NH₂ | Pr | Me | H | 7-N(Pen)CO(4-Cl—Ph) |
| VI-37 | —SO₂NHCO—(CH₂)₅NH₂ | Pr | Me | H | 7-N(Pr)CO₂—ⁱBu |
| VI-38 | —SO₂NHCO—(CH₂)₅NH₂ | Pr | cʸPr | H | 7-ⁱPr |
| VI-39 | —SO₂NHCO—(CH₂)₅NH₂ | Pr | cʸPr | H | 7-SO₂Me |

10. A pharmaceutical composition useful in the treatment of hypertension which comprises a pharmaceutically acceptable carrier and a pharmaceutically effective amount of a compound of claim 1.

11. A method of treating hypertension which comprises administering to a patient in need of such treatment a pharmaceutically effective amount of a compound of claim 1.

12. An ophthalmological formulation for the treatment of ocular hypertension comprising an ophthalmologically acceptable carrier and an effective ocular antihypertensive amount of a compound of claim 1.

13. A method of treating ocular hypertension comprising administering to a patient in need of such treatment an effective ocular antihypertensive amount of a compound of claim 1.

14. A method of treating cognitive dysfunction, anxiety, or depression comprising administering to a patient in need of such treatment an effective therapeutic amount of a compound of claim 1.

* * * * *